US 7,998,984 B2

(12) United States Patent
Hansen et al.

(10) Patent No.: US 7,998,984 B2
(45) Date of Patent: Aug. 16, 2011

(54) 2-PYRIDONE DERIVATIVES FOR THE TREATMENT OF DISEASE OR CONDITION IN WHICH INHIBITION OF NEUTROPHIL ELASTASE ACTIVITY IS BENEFICIAL

(75) Inventors: Peter Hansen, Lund (SE); Karolina Lawitz, Lund (SE); Matti Lepistö, Lund (SE); Hans Lönn, Lund (SE); Asim Ray, Lund (SE)

(73) Assignee: AstraZeneca AB, Södertälje (SE)

( * ) Notice: Subject to any disclaimer, the term of this patent is extended or adjusted under 35 U.S.C. 154(b) by 0 days.

(21) Appl. No.: 12/299,879

(22) PCT Filed: May 7, 2007

(86) PCT No.: PCT/SE2007/000441
§ 371 (c)(1),
(2), (4) Date: Jan. 29, 2009

(87) PCT Pub. No.: WO2007/129962
PCT Pub. Date: Nov. 15, 2007

(65) Prior Publication Data
US 2009/0131486 A1 May 21, 2009

Related U.S. Application Data

(60) Provisional application No. 60/798,786, filed on May 8, 2006.

(51) Int. Cl.
*A61K 31/44* (2006.01)
*A61K 31/47* (2006.01)
*C07D 413/00* (2006.01)
*C07D 401/00* (2006.01)

(52) U.S. Cl. ............... 514/340; 546/270.4; 546/275.4; 546/272.4; 514/342; 514/341

(58) Field of Classification Search ............... 546/275.4, 546/271.4, 270.4; 514/341, 342, 340
See application file for complete search history.

(56) References Cited

U.S. PATENT DOCUMENTS

| | | | |
|---|---|---|---|
| 4,181,658 A | 1/1980 | Hitzel et al. | |
| 4,186,200 A | 1/1980 | Kubo et al. | |
| 5,441,960 A | 8/1995 | Bernstein et al. | |
| 5,521,179 A | 5/1996 | Bernstein et al. | |
| 6,028,081 A | 2/2000 | Sada et al. | |
| 6,977,266 B2 | 12/2005 | Tada et al. | |
| 6,979,690 B2 | 12/2005 | Gymer et al. | |
| 2004/0082619 A1 | 4/2004 | Tada et al. | |
| 2004/0235761 A1 | 11/2004 | Furuta et al. | |
| 2005/0101590 A1 | 5/2005 | Yasui et al. | |
| 2006/0021169 A1 | 2/2006 | Choo | |
| 2006/0052411 A1 | 3/2006 | Tada et al. | |
| 2006/0100249 A1 | 5/2006 | Smith | |
| 2006/0270666 A1 | 11/2006 | Bladh et al. | |
| 2007/0213323 A1 | 9/2007 | Imogai et al. | |
| 2009/0131486 A1 | 5/2009 | Hansen et al. | |
| 2009/0209555 A1 | 8/2009 | Hansen et al. | |
| 2010/0216843 A1 | 8/2010 | Briggner et al. | |

FOREIGN PATENT DOCUMENTS

| | | |
|---|---|---|
| EP | 0008864 A1 | 3/1980 |
| EP | 1357111 B1 | 10/2003 |
| EP | 1465626 A2 | 10/2004 |
| GB | 2383326 A | 6/2003 |
| GB | 2392910 A | 3/2004 |
| JP | 2-152966 A | 6/1990 |
| WO | 98/24780 A2 | 6/1998 |
| WO | 02/053543 A1 | 7/2002 |
| WO | WO-03/015798 A1 | 2/2003 |
| WO | 1300396 | 4/2003 |
| WO | WO 03/047577 | 6/2003 |
| WO | WO-03/047577 A2 | 6/2003 |
| WO | WO-03/070277 A1 | 8/2003 |
| WO | WO 2004/020410 | 3/2004 |
| WO | WO 2004/043924 | 5/2004 |
| WO | 2005/021512 A1 | 3/2005 |
| WO | WO 2005/021509 | 3/2005 |
| WO | WO 2005/026123 | 3/2005 |
| WO | WO 2005/026124 | 3/2005 |
| WO | 2005/082864 A1 | 9/2005 |
| WO | WO 2005/080372 | 9/2005 |

(Continued)

OTHER PUBLICATIONS

Bauer and Weber, Justus liebigs Annalen der Chemie, 1972, vol. 762, pp. 73-82. "Close compound but not within scope!" Beilstein Institute for Organic Chemistry, XP002481053 & KHIM Geterotsikl Soedin vol. 34(1) 1998, pp. 73-76.
Chughtai, et al., J. Aerosol Med., Dec. 1, 2004, 17(4): 289-298.
Europ. Resp. Soc., Feb. 13, 2007, http://www.newtocopd.com/currentaffairsnews/list751_item17680.aspx, downloaded Jan. 16, 2008.
Friedman, Clinical Cornerstone, COPD, vol. 5, No. 1, 45-51, 2004.
Harayama et al, JCS Perkin I, 1987, 75-83.
Ohbayashi, Expert Opinion on Investigational Drugs, 2002, vol. 11(7), pp. 965-980. NEI and diseases.
Ohbayashi, H, Expert Opinion on Therapeutic Patents, 2005, vol. 15(7), pp. 759-771.
Ohbayashi, The Investigational Drugs Journal, 2002, vol. 5(9), pp. 910-923. NEI and diseases.

(Continued)

*Primary Examiner* — Janet L Andres
*Assistant Examiner* — Binta M Robinson
(74) *Attorney, Agent, or Firm* — Connolly Bove Lodge & Hutz LLP

(57) ABSTRACT

The invention provides compounds of formula (I)

wherein $R^1$, $R^3$, $R^4$, $R^5$, $R^6$, $R^{14}$, X and W are as defined in the specification and optical isomers, racemates and tautomers thereof, and pharmaceutically acceptable salts thereof; together with processes for their preparation, pharmaceutical compositions containing them and their use in therapy. The compounds are inhibitors of human neutrophil elastase.

13 Claims, No Drawings

FOREIGN PATENT DOCUMENTS

| WO | WO-2006/004636 A2 | 1/2006 |
|---|---|---|
| WO | WO-2006/030032 A1 | 3/2006 |
| WO | 2006/082412 A2 | 8/2006 |
| WO | WO 2006/098683 | 9/2006 |
| WO | WO 2006/098684 | 9/2006 |
| WO | WO-2006/116713 A1 | 11/2006 |
| WO | 2006/136857 A1 | 12/2006 |
| WO | 2007/107706 A2 | 9/2007 |
| WO | 2007/129060 A1 | 11/2007 |
| WO | 2007/129963 A1 | 11/2007 |
| WO | 2008/030158 A1 | 3/2008 |
| WO | 2008/104752 A1 | 9/2008 |
| WO | WO-2008/104752 A1 | 9/2008 |
| WO | 2009/058076 A1 | 5/2009 |
| WO | 2009/061271 A1 | 5/2009 |
| WO | WO-2010/094964 A1 | 8/2010 |

OTHER PUBLICATIONS

Okayama, et al., J. Anesth (2006) 20;6-10.
Sato et al., Surgical Oncology, 2006, vol. 15, pp. 217-222. NEI and diseases.
Shimizu, et al., Am. J. Respir. Crit. Care Med., vol. 161, #5, May 2000, 1648-1654.
STN International, File CAPLUS, CAPLUS accession No. 1990:611864, Document No. 113:211864, Otsuka Pharmaceutical Co., Ltd.: "4-Hydroxycarbostyrils as anti-inflammatory and antiallergy agents"; & JP, A2, 02152966, 19900612.
STN International, File CAPLUS, CAPLUS accession No. 1995:456529, Document No. 123:198678, Ukrainets, I.V. et al; "4-Hydroxy-2-quinolones. 23. N-(2-Thiazolyl)amides of 1-substituted 4-hydroxy-2oxoquinoline-3-carboxylic acids—a new group of potential anti-inflammatory drugs": & Khimiya Geterotsiklicheskikh Soedinenii (1994), (10), 1397-9.
Ukrainets et al. "4-Hydroxy-2-quinolones.23.N-(2-Thiazolyl)amides of 1-substituted 4-hydroxy-2-oxoquinoline-3-carboxylic acids—a new group of potential antiinflammatory drugs" Chemistry of Heterocyclic Compounds, A translation of Khimiya Geterotsiklicheskikh Soedinenii, 30(10): 1211-1213 (1994).
Wright, et al., Eur. Respir. J. 2003; 22:77-81.
Zeiher et al, Critical Care Medicine, 2002, vol. 30(5), suppl. S281 to S287. NEI and diseases.
Eistert et al., "Reactions of Quinones and α-Dicarbonyl Compounds with Diazoalkanes, XXIV. Synthesis and Reactions of Substituted Pyrroline-2,3-Diones with Diazoalkanes", *Justus Liebigs Annalen der Chemie*, vol. 6, pp. 1023-1030 (1976).
U.S. Appl. No. 10/569,923, office action dated Apr. 9, 2008.
U.S. Appl. No. 10/569,923, office action dated Dec. 12, 2008.
U.S. Appl. No. 10/534,720, restriction requirement dated Feb. 28, 2008.
U.S. Appl. No. 10/534,720, office action dated Jun. 23, 2008.
U.S. Appl. No. 10/534,720, office action dated Jan. 2, 2009.
U.S. Appl. No. 10/534,720, interview summary dated Jul. 14, 2009.
U.S. Appl. No. 10/569,571, office action dated Sep. 29, 2008.
U.S. Appl. No. 10/569,571, office action dated Mar. 16, 2009.
U.S. Appl. No. 10/569,571, interview summary dated Sep. 28, 2009.
U.S. Appl. No. 10/572,640, office action dated Jan. 21, 2009.
U.S. Appl. No. 10/572,640, interview summary dated Aug. 4, 2009.
U.S. Appl. No. 10/572,706, restriction requirement dated Oct. 29, 2009.
U.S. Appl. No. 10/572,706, non-final rejection dated Feb. 17, 2010.
U.S. Appl. No. 10/572,706, ex-parte quayle action dated Jul. 21, 2010.
U.S. Appl. No. 10/572,706, interview summary dated Nov. 5, 2010.
U.S. Appl. No. 10/572,706, notice of allowance dated Nov. 5, 2010.

2-PYRIDONE DERIVATIVES FOR THE TREATMENT OF DISEASE OR CONDITION IN WHICH INHIBITION OF NEUTROPHIL ELASTASE ACTIVITY IS BENEFICIAL

RELATED APPLICATIONS

The present application is a U.S. National Phase Application of International Application No. PCT/SE2007/000441 (filed May 7, 2007) which claims the benefit of U.S. Provisional Application No. 60/798,786 (filed May 8, 2006), both of which are hereby incorporated by reference in their entirety.

FIELD OF THE INVENTION

The present invention relates to 2-pyridone derivatives, processes for their preparation, pharmaceutical compositions containing them and their use in therapy.

BACKGROUND OF THE INVENTION

Elastases are possibly the most destructive enzymes in the body, having the ability to degrade virtually all connective tissue components. The uncontrolled proteolytic degradation by elastases has been implicated in a number of pathological conditions. Human neutrophil elastase (hNE), a member of the chymotrypsin superfamily of serine proteases is a 33-KDa enzyme stored in the azurophilic granules of the neutrophils. In neutrophils the concentration of NE exceeded 5 mM and its total cellular amount has been estimated to be up to 3 pg. Upon activation, NE is rapidly released from the granules into the extracellular space with some portion remaining bound to neutrophil plasma membrane (See Kawabat et al. 2002, Eur. J. Pharmacol. 451, 1-10). The main intracellular physiological function of NE is degradation of foreign organic molecules phagocytosed by neutrophils, whereas the main target for extracellular elastase is elastin (Janoff and Scherer, 1968, J. Exp. Med. 128, 1137-1155). NE is unique, as compared to other proteases (for example, proteinase 3) in that it has the ability to degrade almost all extracellular matrix and key plasma proteins (See Kawabat et al., 2002, Eur. J. Pharmacol. 451, 1-10). It degrades a wide range of extracellular matrix proteins such as elastin, Type 3 and type 4 collagens, laminin, fibronectin, cytokines, etc. (Ohbayashi, H., 2002, Expert Opin. Investig. Drugs, 11, 965-980). NE is a major common mediator of many pathological changes seen in chronic lung disease including epithelial damage (Stockley, R. A. 1994, Am. J. Resp. Crit. Care Med. 150, 109-113).

The destructive role of NE was solidified almost 40 years ago when Laurell and Eriksson reported an association of chronic airflow obstruction and emphysema with deficiency of serum $\alpha_1$-antitrypsin (Laurell and Eriksson, 1963, Scand. J. Clin. Invest. 15, 132-140). Subsequently it was determined that $\alpha_1$-antitrypsin is the most important endogenous inhibitor of human NE. The imbalance between human NE and endogenous antiprotease is believed to cause excess human NE in pulmonary tissues which is considered as a major pathogenic factor in chronic obstructive pulmonary disease (COPD). The excessive human NE shows a prominent destructive profile and actively takes part in destroying the normal pulmonary structures, followed by the irreversible enlargement of the respiratory airspaces, as seen mainly in emphysema. There is an increase in neutrophil recruitment into the lungs which is associated with increased lung elastase burden and emphysema in $\alpha_1$-proteinase inhibitor-deficient mice (Cavarra et al., 1996, Lab. Invest. 75, 273-280). Individuals with higher levels of the NE-$\alpha_1$ protease inhibitor complex in bronchoalveolar lavage fluid show significantly accelerated decline in lung functions compared to those with lower levels (Betsuyaku et al. 2000, Respiration, 67, 261-267). Instillation of human NE via the trachea in rats causes lung haemorrhage, neutrophil accumulation during acute phase and emphysematous changes during chronic phase (Karaki et al., 2002, Am. J. Resp. Crit. Care Med., 166, 496-500). Studies have shown that the acute phase of pulmonary emphysema and pulmonary haemorrhage caused by NE in hamsters can be inhibited by pre-treatment with inhibitors of NE (Fujie et al., 1999, Inflamm. Res. 48, 160-167).

Neutrophil-predominant airway inflammation and mucus obstruction of the airways are major pathologic features of COPD, including cystic fibrosis and chronic bronchitis. NE impairs mucin production, leading to mucus obstruction of the airways. NE is reported to increase the expression of major respiratory mucin gene, MUC5AC (Fischer, B. M & Voynow, 2002, Am. J. Respir. Cell Biol., 26, 447-452). Aerosol administration of NE to guinea pigs produces extensive epithelial damage within 20 minutes of contact (Suzuki et al., 1996, Am. J. Resp. Crit. Care Med., 153, 1405-1411). Furthermore NE reduces the ciliary beat frequency of human respiratory epithelium in vitro (Smallman et al., 1984, Thorax, 39, 663-667) which is consistent with the reduced mucociliary clearance that is seen in COPD patients (Currie et al., 1984, Thorax, 42, 126-130). The instillation of NE into the airways leads to mucus gland hyperplasia in hamsters (Lucey et al., 1985, Am. Resp. Crit. Care Med., 132, 362-366). A role for NE is also implicated in mucus hypersecretion in asthma. In an allergen sensitised guinea pig acute asthma model an inhibitor of NE prevented goblet cell degranulation and mucus hypersecretion (Nadel et al., 1999, Eur. Resp. J., 13, 190-196). NE has been also shown to play a role in the pathogenesis of pulmonary fibrosis. NE: $\alpha_1$-protenase inhibitor complex is increased in serum of patients with pulmonary fibrosis, which correlates with the clinical parameters in these patients (Yamanouchi et al., 1998, Eur. Resp. J. 11, 120-125). In a murine model of human pulmonary fibrosis, a NE inhibitor reduced bleomycin-induced pulmonary fibrosis (Taooka et al., 1997, Am. J. Resp. Crit. Care Med., 156, 260-265). Furthermore investigators have shown that NE deficient mice are resistant to bleomycin-induced pulmonary fibrosis (Dunsmore et al., 2001, Chest, 120, 35S-36S). Plasma NE level was found to be elevated in patients who progressed to ARDS implicating the importance of NE in early ARDS disease pathogenesis. (Donnelly et al., 1995, Am. J. Res. Crit. Care Med., 151, 428-1433). The antiproteases and NE complexed with antiprotease are increased in lung cancer area (Marchandise et al., 1989, Eur. Resp. J. 2, 623-629). Recent studies have shown that polymorphism in the promoter region of the NE gene are associated with lung cancer development (Taniguchi et al., 2002, Clin. Cancer Res., 8, 1115-1120.

Acute lung injury caused by endotoxin in experimental animals is associated with elevated levels of NE (Kawabata, et al., 1999, Am. J. Resp. Crit. Care, 161, 2013-2018). Acute lung inflammation caused by intratracheal injection of lipopolysaccharide in mice has been shown to elevate the NE activity in bronchoalveolar lavage fluid which is significantly inhibited by a NE inhibitor (Fujie et al., 1999, Eur. J. Pharmacol., 374, 117-125; Yasui, et al., 1995, Eur. Resp. J., 8, 1293-1299). NE also plays an important role in the neutrophil-induced increase of pulmonary microvascular permeability observed in a model of acute lung injury caused by tumour necrosis factor $\alpha$ (TNF$\alpha$) and phorbol myristate acetate (PMA) in isolated perfused rabbit lungs (Miyazaki et al., 1998, Am. J. Respir. Crit. Care Med., 157, 89-94).

A role for NE has also been suggested in monocrotoline-induced pulmonary vascular wall thickening and cardiac hypertrophy (Molteni et al., 1989, Biochemical Pharmacol. 38, 2411-2419). Serine elastase inhibitor reverses the monocrotaline-induced pulmonary hypertension and remodelling in rat pulmonary arteries (Cowan et al., 2000, Nature Medicine, 6, 698-702). Recent studies have shown that serine elastase, that is, NE or vascular elastase are important in cigarette smoke-induced muscularisation of small pulmonary arteries in guinea pigs (Wright et al., 2002, Am. J. Respir. Crit. Care Med., 166, 954-960).

NE plays a key role in experimental cerebral ischemic damage (Shimakura et al., 2000, Brain Research, 858, 55-60), ischemia-reperfusion lung injury (Kishima et al., 1998, Ann. Thorac. Surg. 65, 913-918) and myocardial ischemia in rat heart (Tiefenbacher et al., 1997, Eur. J. Physiol., 433, 563-570). Human NE levels in plasma are significantly increased above normal in inflammatory bowel diseases, for example, Crohn's disease and ulcerative colitis (Adeyemi et al., 1985, Gut, 26, 1306-1311). In addition NE has also been assumed to be involved in the pathogenesis of rheumatoid arthritis (Adeyemi et al., 1986, Rheumatol. Int., 6, 57). The development of collagen induced arthritis in mice is suppressed by a NE inhibitor (Kakimoto et al., 1995, Cellular Immunol. 165, 26-32).

Thus, human NE is known as one of the most destructive serine proteases and has been implicated in a variety of inflammatory diseases. The important endogenous inhibitor of human NE is $\alpha_1$-antitrypsin. The imbalance between human NE and antiprotease is believed to give rise to an excess of human NE resulting in uncontrolled tissue destruction. The protease/antiprotease balance may be upset by a decreased availability of $\alpha_1$-antitrypsin either through inactivation by oxidants such as cigarette smoke, or as a result of genetic inability to produce sufficient serum levels. Human NE has been implicated in the promotion or exacerbation of a number of diseases such as pulmonary emphysema, pulmonary fibrosis, adult respiratory distress syndrome (ARDS), ischemia reperfusion injury, rheumatoid arthritis and pulmonary hypertension.

DISCLOSURE OF THE INVENTION

In accordance with the present invention, there is therefore provided a compound of formula (I)

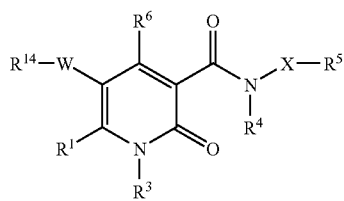

(I)

wherein
$R^1$ represents hydrogen or $C_1$-$C_6$ alkyl;
W represents a 5-membered heterocyclic ring comprising at least one ring heteroatom selected from nitrogen, oxygen and sulphur, wherein at least one of the ring carbon atoms may be optionally replaced by a carbonyl group; and wherein the heterocyclic ring is optionally substituted by at least one substituent selected from halogen, $C_1$-$C_4$ alkyl, $C_1$-$C_4$ alkoxy, CN, OH, $NO_2$, $C_1$-$C_3$ alkyl substituted by one or more F atoms, $C_1$-$C_3$ alkoxy substituted by one or more F atoms, $NR^{10}R^{11}$, $C\equiv CR^{15}$, $CONR^{16}R^{17}$, CHO, $C_2$-$C_4$ alkanoyl, $S(O)_xR^{18}$ and $OSO_2R^{19}$;

$R^{14}$ represents phenyl or a 6-membered heteroaromatic ring comprising 1 to 3 ring nitrogen atoms; said ring being optionally substituted with at least one substituent selected from halogen, $C_1$-$C_4$ alkyl, $C_1$-$C_4$ alkoxy, CN, OH, $NO_2$, $C_1$-$C_3$ alkyl substituted by one or more F atoms, $C_1$-$C_3$ alkoxy substituted by one or more F atoms, $NR^{12}R^{13}$, $C\equiv CR^{30}$, $CONR^{31}R^{32}$, CHO, $C_2$-$C_4$ alkanoyl, $S(O)_pR^{33}$ and $OSO_2R^{34}$;

$R^{10}$, $R^{11}$, $R^{12}$ and $R^{13}$ independently represent H, $C_1$-$C_6$ alkyl, formyl or $C_2$-$C_6$ alkanoyl; or the group —$NR^{10}R^{11}$ or —$NR^{12}R^{13}$ together represents a 5 to 7 membered azacyclic ring optionally incorporating one further heteroatom selected from O, S and $NR^{26}$;

$R^{15}$ and $R^{30}$ independently represent H, $C_1$-$C_3$ alkyl or $Si(CH_3)_3$;

$R^{18}$, $R^{19}$, $R^{33}$ and $R^{34}$ independently represent H or $C_1$-$C_3$ alkyl; said alkyl being optionally substituted by one or more F atoms;

$R^6$ represents H or F;

$R^3$ represents phenyl or a five- or six-membered heteroaromatic ring containing 1 to 3 heteroatoms independently selected from O, S and N; said ring being optionally substituted with at least one substituent selected from halogen, $C_1$-$C_6$ alkyl, cyano, $C_1$-$C_6$ alkoxy, nitro, methylcarbonyl, $NR^{35}R^{36}$, $C_1$-$C_3$ alkyl substituted by one or more F atoms or $C_1$-$C_3$ alkoxy substituted by one or more F atoms;

$R^{35}$ and $R^{36}$ independently represent H or $C_1$-$C_3$ alkyl; said alkyl being optionally further substituted by one or more F atoms;

$R^4$ represents hydrogen or $C_1$-$C_6$ alkyl optionally substituted with at least one substituent selected from fluoro, hydroxyl and $C_1$-$C_6$ alkoxy;

X represents a single bond, O, $NR^{24}$ or a group —$C_1$-$C_6$ alkylene-Y—, wherein Y represents a single bond, oxygen atom, $NR^{24}$ or $S(O)_w$; and said alkylene being optionally further substituted by OH, halogen, CN, $NR^{37}R^{38}$, $C_1$-$C_3$ alkoxy, $CONR^{39}R^{40}$, $CO_2R^{56}$, $SO_2R^{41}$ and $SO_2NR^{42}R^{43}$;

or $R^4$ and X are joined together such that the group —$NR^4X$ together represents a 5 to 7 membered azacyclic ring optionally incorporating one further heteroatom selected from O, S and $NR^{44}$; said ring being optionally substituted by $C_1$-$C_6$ alkyl or $NR^{45}R^{46}$; said alkyl being optionally further substituted by OH;

either $R^5$ represents a monocyclic ring system selected from
i) phenoxy,
ii) phenyl,
iii) a 5- or 6-membered heteroaromatic ring comprising at least one ring heteroatom selected from nitrogen, oxygen and sulphur,
iv) a saturated or partially unsaturated $C_3$-$C_6$ cycloalkyl ring, or
v) a saturated or partially unsaturated 4- to 7-membered heterocyclic ring comprising at least one ring heteroatom selected from oxygen, $S(O)_r$ and $NR^{20}$, wherein at least one of the ring carbon atoms may be optionally replaced by a carbonyl group,
or $R^5$ represents a bicyclic ring system in which the two rings are independently selected from the monocyclic ring systems defined in ii), iii), iv) and v) above, wherein the two rings are either fused together, bonded directly to one another or are separated from one another by a linker group selected from oxygen, $S(O)_t$ or $C_1$-$C_6$ alkylene optionally comprising one or more internal or terminal heteroatoms selected from oxygen, sulphur and $NR^{27}$ and being optionally substituted by at least one substituent selected from hydroxyl, oxo and $C_1$-$C_6$ alkoxy, the monocyclic or bicyclic ring system being optionally substituted by at least one substituent selected from oxygen, CN, OH, $C_1$-$C_6$ allyl, $C_1$-$C_6$ alkoxy, halogen, $NR^{47}R^{48}$, $NO_2$, $OSO_2R^{49}$, $CO_2R^{50}$, $C(=NH)NH_2$, $C(O)NR^{51}R^{52}$, $C(S)NR^{53}R^{54}$, $SC(=NH)NH_2$, $NR^{55}C(=NH)NH_2$, $S(O)_vR^{21}$, $SO_2NR^{56}R^{57}$, $C_1$-$C_3$ alkoxy substituted by one or more F atoms and $C_1$-$C_3$ alkyl substituted by $SO_2R^{58}$ or by one or more F atoms; said $C_1$-$C_6$ alkyl being optionally further substituted with at least one substituent selected from cyano, hydroxyl, $C_1$-$C_6$ alkoxy, $C_1$-$C_6$ alkylthio and —$C(O)NR^{22}R^{23}$;

or $R^5$ may also represent H;

$R^{20}$ represents hydrogen, $C_1$-$C_6$ alkyl, $C_1$-$C_6$ alkylcarbonyl or $C_1$-$C_6$ alkoxycarbonyl;

$R^{21}$ represents hydrogen, $C_1$-$C_6$ alkyl or $C_3$-$C_8$ cycloalkyl; said alkyl or cycloalkyl group being optionally further substituted by one or more substituents selected independently from OH, CN, $C_1$-$C_3$ alkoxy and $CONR^{59}R^{60}$;

$R^{37}$ and $R^{38}$ independently represent H, $C_1$-$C_6$ alkyl, formyl or $C_2$-$C_6$ alkanoyl;

$R^{47}$ and $R^{48}$ independently represent H, $C_1$-$C_6$ alkyl, formyl, $C_2$-$C_6$ alkanoyl, $S(O)_qR^{61}$ or $SO_2NR^{62}R^{63}$; said alkyl group being optionally further substituted by halogen, CN, $C_1$-$C_4$ alkoxy or $CONR^{64}R^{65}$;

$R^{41}$ and $R^{61}$ independently represent H, $C_1$-$C_6$ alkyl or $C_3$-$C_6$ cycloalkyl;

p is 0, 1 or 2;
q is 0, 1 or 2;
r is 0, 1 or 2;
t is 0, 1 or 2;
w is 0, 1 or 2;
x is 0, 1 or 2;
v is 0, 1 or 2;

$R^{16}$, $R^{17}$, $R^{22}$, $R^{23}$, $R^{24}$, $R^{26}$, $R^{27}$, $R^{31}$, $R^{32}$, $R^{39}$, $R^{40}$, $R^{42}$, $R^{43}$, $R^{44}$, $R^{45}$, $R^{46}$, $R^{49}$, $R^{50}$, $R^{51}$, $R^{52}$, $R^{53}$, $R^{54}$, $R^{55}$, $R^{56}$, $R^{57}$, $R^{58}$, $R^{59}$, $R^{60}$, $R^{62}$, $R^{63}$, $R^{64}$, $R^{65}$ and $R^{66}$ each independently represent hydrogen or $C_1$-$C_6$ alkyl;

or a pharmaceutically acceptable salt thereof.

In the context of the present specification, unless otherwise stated, an alkyl, alkenyl or alkynyl substituent group or an alkyl moiety in a substituent group may be linear or branched. Similarly, an alkylene group may be linear or branched.

In the definition of W, the 5-membered heterocyclic ring system may have alicyclic or aromatic properties and may thus be a saturated ring system or a partially unsaturated ring system or a fully unsaturated ring system.

$R^1$ represents hydrogen or $C_1$-$C_6$ alkyl (e.g. methyl, ethyl, n-propyl, isopropyl, n-butyl, isobutyl, tert-butyl, n-pentyl or n-hexyl).

In one embodiment of the invention, $R^1$ represents a $C_1$-$C_4$ or $C_1$-$C_2$ alkyl group, in particular a methyl group.

W represents a 5-membered heterocyclic ring comprising at least one ring heteroatom selected from nitrogen, oxygen and sulphur, wherein at least one of the ring carbon atoms may be optionally replaced by a carbonyl group; and wherein the heterocyclic ring is optionally substituted by at least one substituent selected from halogen (e.g. fluorine, chlorine, bromine or iodine), $C_1$-$C_4$ alkyl (e.g. methyl, ethyl, n-propyl, isopropyl, n-butyl, isobutyl or tert-butyl), $C_1$-$C_4$ alkoxy (e.g. methoxy, ethoxy, n-propoxy, isopropoxy, n-butoxy, isobutoxy or tert-butoxy), cyano, OH, $NO_2$, $C_1$-$C_3$ alkyl substituted by one or more F atoms (e.g. $CH_2F$, $CHF_2$, $CF_3$, $CH_2CH_2F$, $CH_2CF_3$, $CF_2CF_3$, $CH(CF_3)_2$ and $CH_2CH_2CF_3$), $C_1$-$C_3$ alkoxy substituted by one or more F atoms (e.g. $OCH_2F$, $OCHF_2$, $OCF_3$, $OCH_2CH_2F$, $OCH_2CF_3$, $OCF_2CF_3$, $OCH(CF_3)_2$ and $OCH_2CH_2CF_3$), $NR^{10}R^{11}$, $C\equiv CR^{15}$—$C(O)NR^{16}R^{17}$, CHO, $C_2$-$C_4$ alkanoyl (e.g. methylcarbonyl (acetyl), ethylcarbonyl, n-propylcarbonyl or isopropylcarbonyl), —$S(O)_xR^{18}$, and $OSO_2R^{19}$.

In one embodiment, the group $R^{14}$ and the 2-pyridone ring are bonded to the 5-membered ring W in a 1,2-relationship.

In one embodiment, W represents a 5-membered heteroaromatic ring, especially an unsubstituted 5-membered heteroaromatic ring.

Examples of 5-membered heterocyclic ring systems that may be used, which may be saturated or partially unsaturated or fully unsaturated include any one of pyrrolidinyl, tetrahydrofuranyl, pyrroline, imidazolidinyl, imidazolinyl, pyrazolidinyl, pyrazolinyl, pyrrolidinonyl, imidazolidinonyl, oxazolyl, pyrazolyl, thiazolidinyl, thienyl, isoxazolyl, isothiazolyl, thiadiazolyl, pyrrolyl, furanyl, thiazolyl, imidazolyl, furazanyl, triazolyl and tetrazolyl.

Preferred ring systems for group W include pyrazolyl, thiazolyl, oxazolyl and imidazolyl.

In one embodiment, W represents pyrazolyl, triazolyl, thiazolyl, oxazolyl or imidazolyl.

$R^{14}$ represents phenyl or a 6-membered heteroaromatic ring comprising 1 to 3 (e.g. one, two or three) ring nitrogen atoms; said ring being optionally substituted with at least one (e.g. one, two, three or four) substituent selected from halogen (e.g. fluorine, chlorine, bromine or iodine), $C_1$-$C_4$ alkyl (e.g. methyl, ethyl, n-propyl, isopropyl, n-butyl, isobutyl or tert-butyl), $C_1$-$C_4$ alkoxy (e.g. methoxy, ethoxy, n-propoxy, isopropoxy, n-butoxy, isobutoxy or tert-butoxy), CN, OH, $NO_2$, $C_1$-$C_3$ alkyl substituted by one or more F atoms (e.g. $CH_2F$, $CHF_2$, $CF_3$, $CH_2CH_2F$, $CH_2CF_3$, $CF_2CF_3$, $CH(CF_3)_2$ and $CH_2CH_2CF_3$), $C_1$-$C_3$ alkoxy substituted by one or more F atoms (e.g. $OCH_2F$, $OCHF_2$, $OCF_3$, $OCH_2CH_2F$, $OCH_2CF_3$, $OCF_2CF_3$, $OCH(CF_3)_2$ and $OCH_2CH_2CF_3$), $NR^{12}R^{13}$, $C\equiv CR^{30}$, $CONR^{31}R^{32}$, CHO, $C_2$-$C_4$ alkanoyl (e.g. methylcarbonyl (acetyl), ethylcarbonyl, n-propylcarbonyl or isopropylcarbonyl), $S(O)_pR^{33}$ and $OSO_2R^{34}$.

Examples of a 6-membered heteroaromatic ring comprising 1 to 3 ring nitrogen atoms include pyridinyl, pyrimidinyl, pyridazinyl, pyrazinyl and triazinyl. A preferred ring system is pyridinyl.

In one embodiment, one substituent on the aromatic ring of group $R^{14}$ should be in the 4-(para) position relative to group W.

In one embodiment of the invention, $R^{14}$ represents phenyl or a 6-membered heteroaromatic ring comprising 1 to 3 ring nitrogen atoms; said ring being optionally substituted with at least one substituent selected from F, Cl, CN and $CF_3$.

In an embodiment of the invention, $R^{14}$ represents phenyl or pyridinyl; said ring being optionally substituted with at least one substituent selected from F, Cl, CN and $CF_3$.

In an embodiment of the invention, $R^{14}$ represents a phenyl or pyridinyl group optionally substituted with one or two substituents independently selected from F, Cl, CN and $CF_3$.

In an embodiment of the invention, $R^{14}$ represents phenyl or pyridinyl; said ring being 4-(para) substituted with F, Cl or CN and optionally further substituted.

In an embodiment of the invention, $R^{14}$ represents phenyl or pyridinyl; said ring being 4-(para) substituted with F, Cl or CN.

In one embodiment, $R^6$ represents H.

$R^3$ represents phenyl or a five- or six-membered heteroaromatic ring containing 1 to 3 (e.g. one, two or three) heteroatoms independently selected from O, S and N; said ring being optionally substituted with at least one (e.g. one, two, three or four) substituent selected from halogen (e.g. fluorine, chlorine, bromine or iodine), $C_1$-$C_6$ alkyl (e.g. methyl, ethyl, n-propyl, isopropyl, n-butyl, isobutyl, tert-butyl, n-pentyl or n-hexyl), cyano, $C_1$-$C_6$ alkoxy (e.g. methoxy, ethoxy, n-propoxy, isopropoxy, n-butoxy, isobutoxy, tert-butoxy, n-pentoxy or n-hexoxy), nitro, methylcarbonyl, $NR^{35}R^{36}$, $C_1$-$C_3$ alkyl substituted by one or more F atoms (e.g. $CH_2F$, $CHF_2$, $CF_3$, $CH_2CH_2F$, $CH_2CF_3$, $CF_2CF_3$, $CH(CF_3)_2$ and $CH_2CH_2CF_3$) and $C_1$-$C_3$ alkoxy substituted by one or more F atoms (e.g. $OCH_2F$, $OCHF_2$, $OCF_3$, $OCH_2CH_2F$, $OCH_2CF_3$, $OCF_2CF_3$, $OCH(CF_3)_2$ and $OCH_2CH_2CF_3$).

In one embodiment, $R^3$ represents a phenyl or pyridinyl ring substituted with at least one is substituent (e.g. one, two or three substituents) independently selected from halogen, cyano, nitro, methyl, trifluoromethyl and methylcarbonyl.

In one embodiment, $R^3$ represents a phenyl group substituted with one or two substituents independently selected from fluorine, chlorine, cyano, nitro and trifluoromethyl.

In another embodiment, $R^3$ represents a phenyl group substituted with one or two substituents independently selected from fluorine, chlorine and trifluoromethyl.

In still another embodiment, $R^3$ represents a phenyl group substituted with a trifluoromethyl substituent (preferably in the meta position).

In still another embodiment, $R^3$ represents a phenyl group substituted in the meta position with Br, Cl, $CF_3$ or CN.

$R^4$ represents hydrogen or $C_1$-$C_6$ alkyl (e.g. methyl, ethyl, n-propyl, isopropyl, n-butyl, isobutyl, tert-butyl, n-pentyl or n-hexyl) optionally substituted with at least one substituent (e.g. one or two substituents) independently selected from fluoro, hydroxyl and $C_1$-$C_6$ alkoxy (e.g. methoxy, ethoxy, n-propoxy, isopropoxy, n-butoxy, isobutoxy, tert-butoxy, n-pentoxy or n-hexoxy).

In one embodiment, $R^4$ represents hydrogen or $C_1$-$C_4$ alkyl optionally substituted with one or two substituents independently selected from hydroxyl and $C_1$-$C_4$ alkoxy.

In another embodiment, $R^4$ represents hydrogen.

In one embodiment of the invention, X represents a single bond or a group —$C_1$-$C_6$ alkylene-Y—, wherein Y represents a single bond, oxygen atom, $NR^{24}$ or $S(O)_w$; said alkylene being optionally further substituted by OH, halogen, CN, $NR^{37}R^{38}$, $C_1$-$C_3$ alkoxy, $CONR^{39}R^{40}$, $CO_2R^{66}$, $SO_2R^{41}$ and $SO_2NR^{42}R^{43}$.

In one embodiment of the invention, X represents a single bond or a group —$C_1$-$C_6$ alkylene-Y—, wherein Y represents a single bond, oxygen atom, $NR^{24}$ or $S(O)_w$; said alkylene being optionally further substituted by OH, halogen, CN, $NR^{37}R^{38}$, $C_1$-$C_3$ alkoxy, $CONR^{39}R^{40}$, $SO_2R^{41}$ and $SO_2NR^{42}R^{43}$.

In an embodiment of the invention, X represents a group —$C_1$-$C_6$ alkylene-Y— and Y represents a single bond and the alkylene moiety is a linear or branched $C_1$-$C_6$ or $C_1$-$C_4$ or $C_1$-$C_2$ alkylene, optionally substituted by OH, halogen, CN, $CO_2R^{66}$ or $C_1$-$C_3$ alkoxy.

In an embodiment of the invention, X represents a group —$C_1$-$C_6$ alkylene-Y— and Y represents a single bond and the alkylene moiety is a linear or branched $C_1$-$C_6$ or $C_1$-$C_4$ or $C_1$-$C_2$ alkylene, optionally substituted by OH, halogen, CN or $C_1$-$C_3$ alkoxy.

In another embodiment of the invention, X represents unsubstituted $C_1$-$C_2$ alkylene, particularly methylene.

In another embodiment of the invention, X represents a single bond.

In one embodiment of the invention, $R^4$ and X are joined together such that the group —$NR^4X$ together represents a 5 to 7 membered azacyclic ring optionally incorporating one further heteroatom selected from O, S and $NR^{44}$; said ring being optionally substituted by $C_1$-$C_6$ alkyl or $NR^{45}R^{46}$; said alkyl being optionally further substituted by OH.

Examples of a 5 to 7 membered azacyclic ring optionally incorporating one further heteroatom selected from O, S and $NR^{44}$ include pyrrolidine, piperidine, piperazine, morpholine and perhydroazepine.

$R^5$ represents a monocyclic ring system selected from
i) phenoxy,
ii) phenyl,
iii) a 5- or 6-membered heteroaromatic ring comprising at least one ring heteroatom (e.g. one, two, three or four ring heteroatoms) independently selected from nitrogen, oxygen and sulphur,
iv) a saturated or partially unsaturated $C_3$-$C_6$ cycloalkyl ring, or
v) a saturated or partially unsaturated 4- to 7-membered heterocyclic ring comprising at least one ring heteroatom (e.g. one, two, three or four ring heteroatoms) independently selected from oxygen, $S(O)_r$ and $NR^{20}$, wherein at least one of the ring carbon atoms may be optionally replaced by a carbonyl group,
or $R^5$ represents a bicyclic ring system in which the two rings are independently selected from the monocyclic ring systems defined in ii), iii), iv) and v) above, wherein the two rings are either fused together, bonded directly to one another or are separated from one another by a linker group selected from oxygen, $S(O)_t$ or $C_1$-$C_6$ alkylene optionally comprising one or more (e.g. one or two) internal or terminal heteroatoms selected from oxygen, sulphur and $NR^{27}$ and being optionally substituted by at least one substituent (e.g. one or two substituents) independently selected from hydroxyl, oxo and $C_1$-$C_6$ alkoxy (e.g. methoxy, ethoxy, n-propoxy, isopropoxy, n-butoxy, isobutoxy, tert-butoxy, n-pentoxy or n-hexoxy);

the monocyclic or bicyclic ring system being optionally substituted (on a ring atom) by at least one substituent (e.g. one, two or three substituents) independently selected from oxygen (e.g. to form an N-oxide), CN, OH, $C_1$-$C_6$ alkyl (e.g. methyl, ethyl, n-propyl, isopropyl, n-butyl, isobutyl, tert-butyl, n-pentyl or n-hexyl), $C_1$-$C_6$ alkoxy (e.g. methoxy, ethoxy, n-propoxy, isopropoxy, n-butoxy, isobutoxy, tert-butoxy, n-pentoxy or n-hexoxy), halogen (e.g. fluorine, chlorine, bromine or iodine), $NR^{47}R^{48}$, $NO_2$, $OSO_2R^{49}$, $CO_2R^{50}$, C(=NH)$NH_2$, C(O)$NR^{51}R^{52}$, C(S)$NR^{53}R^{54}$, SC(=NH)$NH_2$, $NR^{55}$C(=NH)$NH_2$, —S(O)$_v$$R^{21}$, $SO_2NR^{56}R^{57}$, $C_1$-$C_3$ alkoxy substituted by one or more F atoms (e.g. $OCH_2F$, $OCHF_2$, $OCF_3$, $OCH_2CH_2F$, $OCH_2CF_3$, $OCF_2CF_3$, $OCH(CF_3)_2$ and $OCH_2CH_2CF_3$) and $C_1$-$C_3$ alkyl substituted by $SO_2R^{58}$ or by one or more F atoms (e.g. $CH_2SO_2R^{58}$, $CH_2CH_2SO_2R^{58}$, $CH(SO_2R^{58})CH_3$, $CH_2F$, $CHF_2$, $CF_3$, $CH_2CH_2F$, $CH_2CF_3$, $CF_2CF_3$, $CH(CF_3)_2$ and $CH_2CH_2CF_3$); said $C_1$-$C_6$ alkyl being optionally further substituted with at least one substituent selected from cyano, hydroxyl, $C_1$-$C_6$ alkoxy (e.g. methoxy, ethoxy, n-propoxy, isopropoxy, n-butoxy, isobutoxy, tert-butoxy, n-pentoxy or n-hexoxy), $C_1$-$C_6$ alkylthio (e.g. methylthio, ethylthio, n-propylthio, isopropylthio, n-butylthio, isobutylthio, tert-butylthio, n-pentylthio or n-hexylthio) and —C(O)$NR^{22}R^{23}$; or $R^5$ may also represent hydrogen.

Examples of a 5- or 6-membered heteroaromatic ring include furanyl, thienyl, pyrrolyl, oxazolyl, 1,2,4-oxadiazolyl, 1,3,4-oxadiazolyl, isoxazolyl, imidazolyl, pyrazolyl, thiazolyl, triazolyl, tetrazolyl, thiadiazolyl, pyridinyl, pyrimidinyl and pyrazinyl. Preferred heteroaromatic rings include isoxazolyl, pyridinyl, imidazolyl and triazolyl.

Unless otherwise indicated, a "saturated or partially unsaturated $C_3$-$C_6$ cycloalkyl ring" denotes a 3- to 6-membered non-aromatic cycloalkyl ring optionally incorporating one or more double bonds, examples of which include cyclopropyl, cyclobutyl, cyclopentyl, cyclohexyl, cyclopentenyl and cyclohexenyl. A preferred cycloalkyl ring is cyclopropyl.

Unless otherwise indicated, a "saturated or partially unsaturated 4- to 7-membered heterocyclic ring" as specified above denotes a 4- to 7-membered non-aromatic heterocyclic ring optionally incorporating one or more double bonds and optionally incorporating a carbonyl group, examples of which include tetrahydrofuranyl, tetramethylenesulfonyl, tetrahydropyranyl, 4-oxo-4H-pyranyl (4H-pyran-4-onyl), pyrrolidinyl, 3-pyrrolinyl, imidazolidinyl, 1,3-dioxolanyl (1,3-dioxacyclopentanyl), piperidinyl, piperazinyl, morpholinyl, perhydroazepinyl (hexamethylene iminyl), pyrrolidonyl and piperidonyl. A preferred saturated or partially unsaturated 4- to 7-membered heterocyclic ring is pyrrolidonyl.

Examples of bicyclic ring systems in which the two rings are either fused together, bonded directly to one another or are separated from one another by a linker group include biphenyl, thienylphenyl, pyrazolylphenyl, phenoxyphenyl, phenylcyclopropyl, naphthyl, indanyl, quinolyl, tetrahydroquinolyl, benzofuranyl, indolyl, isoindolyl, indolinyl, benzofuranyl, benzothienyl, indazolyl, benzimidazolyl, benzthiazolyl, purinyl, isoquinolyl, chromanyl, indenyl, quinazolyl, quinoxalyl, chromanyl, isocromanyl, 3H-indolyl, 1H-indazolyl, quinuclidyl, tetrahydronaphthyl, dihydrobenzofuranyl, morpholine-4-ylphenyl, 1,3-benzodioxolyl, 2,3-dihydro-1,4-benzodioxinyl, 1,3-benzodioxinyl and 3,4-dihydro-isochromenyl.

In an embodiment of the invention, $R^5$ represents a substituted monocyclic ring system as defined above.

In another embodiment of the invention, $R^5$ represents a substituted bicyclic ring system as defined above.

In another embodiment of the invention, $R^5$ represents H.

In a further embodiment of the invention, $R^5$ represents a monocyclic ring system selected from
i) phenoxy,
ii) phenyl,
iii) a 5- or 6-membered heteroaromatic ring comprising one or two ring heteroatoms independently selected from nitrogen, oxygen and sulphur,
iv) a saturated or partially unsaturated $C_3$-$C_6$ cycloalkyl ring, or
v) a saturated or partially unsaturated 4- to 7-membered heterocyclic ring comprising one or two ring heteroatoms independently selected from oxygen, $S(O)_r$ and $NR^{20}$, wherein at least one of the ring carbon atoms may be optionally replaced by a carbonyl group;
or $R^5$ represents a bicyclic ring system in which the two rings are independently selected from the monocyclic ring systems defined in ii), iii), iv) and v) above, wherein the two rings are either fused together, bonded directly to one another or are separated from one another by a linker group selected from oxygen, methylene and $S(O)_r$;
the monocyclic or bicyclic ring system being substituted by one or two substituents independently selected from OH, —$S(O)_v R^{21}$ and $C_1$-$C_4$ alkyl.

In a still further embodiment of the invention, $R^5$ represents a monocyclic ring system selected from phenyl or a 5- or 6-membered heteroaromatic ring comprising one or two ring heteroatoms independently selected from nitrogen and oxygen, the monocyclic ring system being substituted by one or two substituents independently selected from OH, —$S(O)_v R^{21}$ and $C_1$-$C_4$ alkyl.

In a still further embodiment of the invention, $R^5$ represents phenyl or pyridinyl substituted by —$S(O)_v R^{21}$ wherein v represents the integer 2.

In a still further embodiment of the invention, $R^5$ represents phenyl substituted by one or two substituents independently selected from OH, —$S(O)_v R^{21}$ and $C_1$-$C_4$ alkyl.

In a still further embodiment of the invention, $R^5$ represents H.

In a still further embodiment of the invention, $R^5$ represents an unsubstituted $C_3$-$C_6$ cycloalkyl ring, particularly cyclopropyl.

In one embodiment, x is 2.
In one embodiment, p is 2.
In one embodiment, $R^{10}$ and $R^{11}$ independently represent H, $C_1$-$C_3$ alkyl or $C_2$-$C_3$ alkylcarbonyl.
In one embodiment, $R^{12}$ and $R^{13}$ independently represent H, $C_1$-$C_3$ alkyl or $C_2$-$C_3$ alkylcarbonyl.
In a further embodiment, $R^{20}$ represents hydrogen, methyl, ethyl, methylcarbonyl (acetyl), ethylcarbonyl, methoxycarbonyl or ethoxycarbonyl.
In one embodiment, v is 2.

$R^{21}$ represents hydrogen, $C_1$-$C_6$ allyl (e.g. methyl, ethyl, n-propyl, isopropyl, n-butyl, isobutyl, tert-butyl, n-pentyl or n-hexyl) or $C_3$-$C_8$ cycloalkyl (cyclopropyl, cyclobutyl, cyclopentyl, cyclohexyl, cycloheptyl or cyclooctyl); said alkyl or cycloalkyl group being optionally further substituted by one or more substituents selected independently from OH, CN, $C_1$-$C_3$ alkoxy and $CONR^{59}R^{60}$.

In an embodiment according to the invention, $R^{21}$ represents $C_1$-$C_4$ alkyl or $C_3$-$C_6$ cycloalkyl.

In another embodiment, $R^{21}$ represents $C_1$-$C_3$ alkyl (particularly methyl, ethyl or isopropyl) or cyclopropyl.

In another embodiment, $R^{41}$ represents $C_1$-$C_3$ alkyl (particularly methyl, ethyl or isopropyl) or cyclopropyl.

In an embodiment of the invention, $R^{15}$, $R^{16}$, $R^{17}$, $R^{18}$, $R^{19}$, $R^{30}$, $R^{31}$, $R^{34}$, $R^{35}$, $R^{36}$, $R^{37}$, $R^{38}$, $R^{47}$, $R^{48}$, $R^{61}$, $R^{22}$, $R^{23}$, $R^{24}$, $R^{26}$, $R^{27}$, $R^{31}$, $R^{32}$, $R^{39}$, $R^{40}$, $R^{42}$, $R^{43}$, $R^{44}$, $R^{45}$, $R^{46}$, $R^{49}$, $R^{50}$, $R^{51}$, $R^{52}$, $R^{53}$, $R^{54}$, $R^{55}$, $R^{56}$, $R^{57}$, $R^{58}$, $R^{59}$, $R^{60}$, $R^{62}$, $R^{63}$, $R^{64}$, $R^{65}$ and $R^{66}$ each independently represent hydrogen or $C_1$-$C_3$ alkyl, particularly methyl, ethyl, 1-propyl or 2-propyl.

In an embodiment of the invention, $R^{15}$, $R^{16}$, $R^{17}$, $R^{18}$, $R^{19}$, $R^{30}$, $R^{33}$, $R^{34}$, $R^{35}$, $R^{36}$, $R^{37}$, $R^{38}$, $R^{47}$, $R^{48}$, $R^{61}$, $R^{22}$, $R^{23}$, $R^{24}$, $R^{26}$, $R^{27}$, $R^{31}$, $R^{32}$, $R^{39}$, $R^{40}$, $R^{42}$, $R^{43}$, $R^{44}$, $R^{45}$, $R^{46}$, $R^{49}$, $R^{50}$, $R^{51}$, $R^{52}$, $R^{53}$, $R^{54}$, $R^{55}$, $R^{56}$, $R^{57}$, $R^{58}$, $R^{59}$, $R^{60}$, $R^{62}$, $R^{63}$, $R^{64}$, $R^{65}$, $R^{66}$ each independently represent hydrogen or methyl.

In an embodiment of the invention, $R^{66}$ represents hydrogen.

In an embodiment of the invention,
$R^1$ represents methyl;
W represents a 5-membered heteroaromatic ring, and the group $R^{14}$ and the 2-pyridone ring are bonded to the 5-membered ring W in a 1,2-relationship;
$R^{14}$ represents phenyl or pyridinyl; said ring being optionally substituted with at least one substituent selected from F, Cl, CN and $CF_3$;
$R^6$ represents H;
$R^3$ represents a phenyl group substituted with one or two substituents independently selected from fluorine, chlorine, cyano, nitro or trifluoromethyl;
$R^4$ represents hydrogen;
X represents unsubstituted $C_1$-$C_2$ alkylene, particularly methylene; and
$R^5$ represents phenyl substituted by one or two substituents independently selected from OH, —$S(O)_v R^{21}$ and $C_1$-$C_4$ alkyl wherein v represents the integer 2.

In an embodiment of the invention, $R^1$ represents methyl;

W represents a 5-membered heteroaromatic ring, and the group $R^{14}$ and the 2-pyridone ring are bonded to the 5-membered ring W in a 1,2-relationship;

$R^{14}$ represents phenyl or pyridinyl; said ring being optionally substituted with at least one substituent selected from F, Cl, CN and $CF_3$;

$R^6$ represents H;

$R^3$ represents a phenyl group substituted with one or two substituents independently selected from fluorine, chlorine, cyano, nitro or trifluoromethyl;

$R^4$ represents hydrogen;

X represents unsubstituted $C_1$-$C_2$ alkylene, particularly methylene; and $R^5$ represents H.

In an embodiment of the invention, $R^1$ represents methyl;

W represents a 5-membered heteroaromatic ring, and the group $R^{14}$ and the 2-pyridone ring are bonded to the 5-membered ring W in a 1,2-relationship;

$R^{14}$ represents phenyl or pyridinyl; said ring being 4-(para) substituted with F, Cl or CN;

$R^6$ represents H;

$R^3$ represents a phenyl group substituted in the meta position with Br, $C_1$, $CF_3$ or CN;

$R^4$ represents hydrogen;

X represents a linear or branched $C_1$-$C_4$ alkylene, optionally substituted by OH, halogen, CN, $CO_2R^{66}$ or $C_1$-$C_3$ alkoxy; and $R^5$ represents H.

Examples of compounds of the invention include
5-[1-(4-cyanophenyl)-1H-pyrazol-5-yl]-N,6-dimethyl-2-oxo-1-[3-(trifluoromethyl)phenyl]-1,2-dihydropyridine-3-carboxamide;
5-[1-(4-cyanophenyl)-1H-pyrazol-5-yl]-6-methyl-N-[4-(methylsulfonyl)benzyl]-2-oxo-1-[3-(trifluoromethyl)phenyl]-1,2-dihydropyridine-3-carboxamide;
5-[2-amino-5-(4-chlorophenyl)-1,3-thiazol-4-yl]-N,6-dimethyl-2-oxo-1-[3-(trifluoromethyl)phenyl]-1,2-dihydropyridine-3-carboxamide;
5-[4-(4-chlorophenyl)-1,3-oxazol-5-yl]-N,6-dimethyl-2-oxo-1-[3-(trifluoromethyl)phenyl]-1,2-dihydropyridine-3-carboxamide;
5-[2-amino-5-(4-cyanophenyl)-1,3-thiazol-4-yl]-N,6-dimethyl-2-oxo-1-[3-(trifluoromethyl)phenyl]-1,2-dihydropyridine-3-carboxamide;
1-(3-chloro-4-fluorophenyl)-5-[1-(4-cyanophenyl)-1H-pyrazol-5-yl]-N,6-dimethyl-2-oxo-1,2-dihydropyridine-3-carboxamide;
5-[2-(4-chloro-phenyl)-2H-pyrazol-3-yl]-6-methyl-2-oxo-1-(3-trifluoromethyl-phenyl)-1,2-dihydro-pyridine-3-carboxylic acid methylamide;
5-[2-(4-fluoro-phenyl)-2H-pyrazol-3-yl]-6-methyl-2-oxo-1-(3-trifluoromethyl-phenyl)-1,2-dihydro-pyridine-3-carboxylic acid methylamide;
5-[3-(4-cyano-phenyl)-3H-[1,2,3]triazol-4-yl]-6-methyl-2-oxo-1-(3-trifluoromethyl-phenyl)-1,2-dihydro-pyridine-3-carboxylic acid methylamide; and
5-[1-(4-cyanophenyl)-1H-1,2,4-triazol-5-yl]-N,6-dimethyl-2-oxo-1-[3-(trifluoromethyl)phenyl]-1,2-dihydropyridine-3-carboxamide;
and pharmaceutically acceptable salts of any one thereof.

The present invention further provides a process for the preparation of a compound of formula (I) or a pharmaceutically acceptable salt thereof as defined above which comprises, (a) reacting a compound of formula (II)

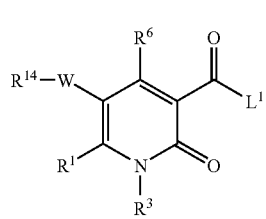

(II)

wherein $L^1$ represents a leaving group (such as halogen or hydroxyl) and $R^1$, $R^3$, $R^6$, $R^{14}$ and W are as defined in formula (I), with a compound of formula

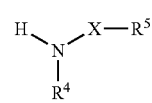

(III)

wherein X, $R^4$ and $R^5$ are as defined in formula (I); or (b) reacting a compound of formula (IV)

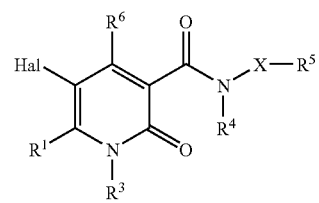

(IV)

wherein Hal represents a halogen atom and X, $R^1$, $R^3$, $R^4$, $R^5$ and $R^6$ are as defined in formula (I), with a nucleophile $R^{14}$—W-M wherein $R^{14}$ and W are as defined in formula (I) and M represents an organo-tin or organo boronic acid group; or (c) when W represents thiazolyl or oxazolyl, reacting a compound of formula (V)

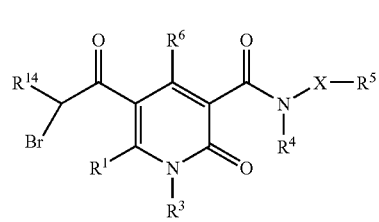

(V)

wherein X, $R^1$, $R^3$, $R^4$, $R^5$, $R^6$ and $R^{14}$ are as defined in formula (I), with thiourea or formamide respectively;

and optionally after (a), (b) or (c) carrying out one or more of the following:

converting the compound obtained to a further compound of the invention forming a pharmaceutically acceptable salt of the compound.

In process (a), the reaction may conveniently be carried out in an organic solvent such as dichloromethane or N-methylpyrrolidinone at a temperature, for example, in the range from 0° C. to the boiling point of the solvent. If necessary or desired, a base and/or a coupling reagent such as HATU (O-(7-Azabenzotriazol-1-yl)-N,N,N',N'-tetramethyluronium hexafluorophosphate), HOAT (1-Hydroxy-7-azabenzotriazole), HOBT (1-Hydroxybenzotriazole hydrate) or DIEA (N,N-Diisopropylethylamine) may be added.

In process (b), the reaction may conveniently be carried out in an organic solvent such as DMF, NMP or toluene or a mixture thereof at elevated temperature (i.e. above ambient temperature, 20° C.), for example, in the range from 50° C. to 150° C. and in the presence of a suitable transition metal catalyst such as bis(tri-t-butylphosphine)palladium. If necessary or desired, a base such as potassium carbonate may be added.

In process (c), the reaction may conveniently be carried out by heating together the two starting materials in a suitable organic solvent such as acetonitrile at a temperature, for example, in the range from 50° C. to 150° C.

Specific processes for the preparation of compounds of Formula (I) are disclosed within the Examples section of the present specification. Such processes form an aspect of the present invention.

The necessary starting materials are either commercially available, are known in the literature or may be prepared using known techniques. Specific processes for the preparation of certain key starting materials are disclosed within the Examples section of the present specification and such processes form an aspect of the present invention. Certain intermediates of formulae (II), (IV) and (V) are novel. Such novel intermediates form another aspect of the invention.

Compounds of formula (I) can be converted into further compounds of formula (I) using standard procedures.

It will be appreciated by those skilled in the art that in the processes of the present invention certain functional groups such as hydroxyl or amino groups may need to be protected by protecting groups. Thus, the preparation of the compounds of formula (I) may involve, at an appropriate stage, the addition and/or removal of one or more protecting groups.

The protection and deprotection of functional groups is described in 'Protective Groups in Organic Chemistry', edited by J. W. F. McOmie, Plenum Press (1973) and 'Protective Groups in Organic Synthesis', $3^{rd}$ edition, T. W. Greene and P. G. M. Wuts, Wiley-Interscience (1999).

The compounds of formula (I) above may be converted to a pharmaceutically acceptable salt thereof, preferably an acid addition salt such as a hydrochloride, hydrobromide, sulphate, phosphate, acetate, fumarate, maleate, tartrate, lactate, citrate, pyruvate, succinate, oxalate, methanesulphonate or p-toluenesulphonate.

Compounds of formula (I) are capable of existing in stereoisomeric forms. It will be understood that the invention encompasses the use of all geometric and optical isomers (including atropisomers) of the compounds of formula (I) and mixtures thereof including racemates. The use of tautomers and mixtures thereof also form an aspect of the present invention. Enantiomerically pure forms are particularly desired.

The compounds of formula (I) and their pharmaceutically acceptable salts have activity as pharmaceuticals, in particular as modulators of serine proteases such as proteinase 3 and pancreatic elastase and, especially, human neutrophil elastase, and may therefore be beneficial in the treatment or prophylaxis of inflammatory diseases and conditions.

The compounds of formula (I) and their pharmaceutically acceptable salts can be used in the treatment of diseases of the respiratory tract such as obstructive diseases of the airways including: asthma, including bronchial, allergic, intrinsic, extrinsic, exercise-induced, drug-induced (including aspirin and NSAID-induced) and dust-induced asthma, both intermittent and persistent and of all severities, and other causes of airway hyper-responsiveness; chronic obstructive pulmonary disease (COPD); bronchitis, including infectious and eosinophilic bronchitis; emphysema; bronchiectasis; cystic fibrosis; sarcoidosis; farmer's lung and related diseases; hypersensitivity pneumonitis; lung fibrosis, including cryptogenic fibrosing alveolitis, idiopathic interstitial pneumonias, fibrosis complicating anti-neoplastic therapy and chronic infection, including tuberculosis and aspergillosis and other fungal infections; complications of lung transplantation; vasculitic and thrombotic disorders of the lung vasculature, and pulmonary hypertension; antitussive activity including treatment of chronic cough associated with inflammatory and secretory conditions of the airways, and iatrogenic cough; acute and chronic rhinitis including rhinitis medicamentosa, and vasomotor rhinitis; perennial and seasonal allergic rhinitis including rhinitis nervosa (hay fever); nasal polyposis; acute viral infection including the common cold, and infection due to respiratory syncytial virus, influenza, coronavirus (including SARS) and adenovirus.

The compounds of formula (I) and their pharmaceutically acceptable salts can also be used in the treatment of diseases of bone and joints such as arthritides associated with or including osteoarthritis/osteoarthrosis, both primary and secondary to, for example, congenital hip dysplasia; cervical and lumbar spondylitis, and low back and neck pain; rheumatoid arthritis and Still's disease; seronegative spondyloarthropathies including ankylosing spondylitis, psoriatic arthritis, reactive arthritis and undifferentiated spondarthropathy; septic arthritis and other infection-related arthopathies and bone disorders such as tuberculosis, including Potts' disease and Poncet's syndrome; acute and chronic crystal-induced synovitis including urate gout, calcium pyrophosphate deposition disease, and calcium apatite related tendon, bursal and synovial inflammation; Behcet's disease; primary and secondary Sjogren's syndrome; systemic sclerosis and limited scleroderma; systemic lupus erythematosus, mixed connective tissue disease, and undifferentiated connective tissue disease; inflammatory myopathies including dermatomyositits and polymyositis; polymalgia rheumatica; juvenile arthritis including idiopathic inflammatory arthritides of whatever joint distribution and associated syndromes, and rheumatic fever and its systemic complications; vasculitides including giant cell arteritis, Takayasu's arteritis, Churg-Strauss syndrome, polyarteritis nodosa, microscopic polyarteritis, and vasculitides associated with viral infection, hypersensitivity reactions, cryoglobulins, and paraproteins; low back pain; Familial Mediterranean fever, Muckle-Wells syndrome, and Familial Hibernian Fever, Kikuchi disease; drug-induced arthalgias, tendonititides, and myopathies.

The compounds of formula (I) and their pharmaceutically acceptable salts can also be used in the treatment of pain and connective tissue remodelling of musculoskeletal disorders due to injury [for example, sports injury] or disease: arthitides (for example rheumatoid arthritis, osteoarthritis, gout or crystal arthropathy), other joint disease (such as intervertebral disc degeneration or temporomandibular joint degeneration), bone remodelling disease (such as osteoporosis, Paget's disease or osteonecrosis), polychondritis, scleroderma, mixed connective tissue disorder, spondyloartbropathies or periodontal disease (such as periodontitis).

The compounds of formula (I) and their pharmaceutically acceptable salts can also be used in the treatment of diseases of skin such as psoriasis, atopic dermatitis, contact dermatitis or other eczematous dermatoses, and delayed-type hypersensitivity reactions; phyto- and photodermatitis; seborrhoeic dermatitis, dermatitis herpetiformis, lichen planus, lichen sclerosus et atrophica, pyoderma gangrenosum, skin sarcoid, discoid lupus erythematosus, pemphigus, pemphigoid, epidermolysis bullosa, urticaria, angioedema, vasculitides, toxic erythemas, cutaneous eosinophilias, alopecia greata, male-pattern baldness, Sweet's syndrome, Weber-Christian syndrome, erythema multiforme; cellulitis, both infective and non-infective; panniculitis; cutaneous lymphomas, non-melanoma skin cancer and other dysplastic lesions; drug-induced disorders including fixed drug eruptions.

The compounds of formula (I) and their pharmaceutically acceptable salts can also be used in the treatment of diseases of the eye such as blepharitis; conjunctivitis, including perennial and vernal allergic conjunctivitis; iritis; anterior and posterior uveitis; choroiditis; autoimmune; degenerative or inflammatory disorders affecting the retina; ophthalmitis including sympathetic ophthalmitis; sarcoidosis; infections including viral, fungal, and bacterial.

The compounds of formula (I) and their pharmaceutically acceptable salts can also be used in the treatment of diseases of the gastrointestinal tract such as glossitis, gingivitis, periodontitis; oesophagitis, including reflux; eosinophilic gastroenteritis, mastocytosis, Crohn's disease, colitis including ulcerative colitis, proctitis, pruritis ani; coeliac disease, irritable bowel syndrome, non-inflammatory diarrhea, and food-related allergies which may have effects remote from the gut (for example, migraine, rhinitis or eczema).

The compounds of formula (I) and their pharmaceutically acceptable salts can also be used in the treatment of diseases of the cardiovascular system such as atherosclerosis, affecting the coronary and peripheral circulation; pericarditis; myocarditis, inflammatory and auto-immune cardiomyopathies including myocardial sarcoid; ischaemic reperfusion injuries; endocarditis, valvulitis, and aortitis including infective (for example syphilitic); vasculitides; disorders of the proximal and peripheral veins including phlebitis and thrombosis, including deep vein thrombosis and complications of varicose veins.

The compounds of formula (I) and their pharmaceutically acceptable salts can also be used in oncology such as in the treatment of common cancers including prostate, breast, lung, ovarian, pancreatic, bowel and colon, stomach, skin and brain tumors and malignancies affecting the bone marrow (including the leukaemias) and lymphoproliferative systems, such as Hodgkin's and non-Hodgkin's lymphoma; including the prevention and treatment of metastatic disease and tumour recurrences, and paraneoplastic syndromes.

In particular, the compounds of formula (I) and their pharmaceutically acceptable salts may be used in the treatment of adult respiratory distress syndrome (ARDS), cystic fibrosis, pulmonary emphysema, bronchitis including chronic bronchitis, bronchiectasis, chronic obstructive pulmonary disease (COPD), pulmonary hypertension, asthma including refractive asthma, rhinitis, psoriasis, ischemia-reperfusion injury, rheumatoid arthritis, osteoarthritis, systemic inflammatory response syndrome (SIRS), chronic wound, cancer, atherosclerosis, peptic ulcers, Crohn's disease, ulcerative colitis and gastric mucosal injury.

More particularly, the compounds of formula (I) and their pharmaceutically acceptable salts may be used in the treatment of chronic obstructive pulmonary disease (COPD), asthma and rhinitis.

Even more particularly, the compounds of formula (I) and their pharmaceutically acceptable salts may be used in the treatment of chronic obstructive pulmonary disease (COPD).

Thus, the present invention provides a compound of formula (I) or a pharmaceutically-acceptable salt thereof as hereinbefore defined for use in therapy.

In a further aspect, the present invention provides the use of a compound of formula (I) or is a pharmaceutically acceptable salt thereof as hereinbefore defined in the manufacture of a medicament for use in therapy.

In a further aspect, the present invention provides the use of a compound of formula (I) or a pharmaceutically acceptable salt thereof as hereinbefore defined in the manufacture of a medicament for the treatment of human diseases or conditions in which modulation of neutrophil elastase activity is beneficial.

In a further aspect, the present invention provides the use of a compound of formula (I) or a pharmaceutically acceptable salt thereof as hereinbefore defined in the manufacture of a medicament for use in the treatment of an inflammatory disease or condition.

In a further aspect, the present invention provides the use of a compound of formula (I) or a pharmaceutically acceptable salt thereof as hereinbefore defined in the manufacture of a medicament for use in treating adult respiratory distress syndrome (ARDS), cystic fibrosis, pulmonary emphysema, bronchitis including chronic bronchitis, bronchiectasis, chronic obstructive pulmonary disease (COPD), pulmonary hypertension, asthma including refractive asthma, rhinitis, psoriasis, ischemia-reperfusion injury, rheumatoid arthritis, osteoarthritis, systemic inflammatory response syndrome (SIRS), chronic wound, cancer, atherosclerosis, peptic ulcers, Crohn's disease, ulcerative colitis or gastric mucosal injury.

In a further aspect, the present invention provides the use of a compound of formula (I) or a pharmaceutically acceptable salt thereof as hereinbefore defined in the manufacture of a medicament for use in treating chronic obstructive pulmonary disease (COPD).

In the context of the present specification, the term "therapy" also includes "prophylaxis" unless there are specific indications to the contrary. The terms "therapeutic" and "therapeutically" should be construed accordingly.

Prophylaxis is expected to be particularly relevant to the treatment of persons who have suffered a previous episode of, or are otherwise considered to be at increased risk of, the disease or condition in question. Persons at risk of developing a particular disease or condition generally include those having a family history of the disease or condition, or those who have been identified by genetic testing or screening to be particularly susceptible to developing the disease or condition.

The invention also provides a method of treating, or reducing the risk of, a disease or condition in which inhibition of neutrophil elastase activity is beneficial which comprises administering to a patient in need thereof a therapeutically effective amount of a compound of formula (I) or a pharmaceutically acceptable salt thereof as hereinbefore defined.

The invention still further provides a method of treating, or reducing the risk of, an inflammatory disease or condition which comprises administering to a patient in need thereof a therapeutically effective amount of a compound of formula (I) or a pharmaceutically acceptable salt thereof as hereinbefore defined.

The invention still further provides a method of treating, or reducing the risk of, adult respiratory distress syndrome (ARDS), cystic fibrosis, pulmonary emphysema, bronchitis including chronic bronchitis, bronchiectasis, chronic obstructive pulmonary disease (COPD), pulmonary hypertension, asthma including refractive asthma, rhinitis, psoriasis, ischemia-reperfusion injury, rheumatoid arthritis, osteoarthritis, systemic inflammatory response syndrome (SIRS), chronic wound, cancer, atherosclerosis, peptic ulcers, Crohn's disease, ulcerative colitis or gastric mucosal injury which comprises administering to a patient in need thereof a therapeutically effective amount of a compound of formula (I) or a pharmaceutically acceptable salt thereof as hereinbefore defined.

The invention still further provides a method of treating, or reducing the risk of, chronic obstructive pulmonary disease (COPD) which comprises administering to a patient in need thereof a therapeutically effective amount of a compound of formula (I) or a pharmaceutically acceptable salt thereof as hereinbefore defined.

For the above-mentioned therapeutic uses the dosage administered will, of course, vary with the compound employed, the mode of administration, the treatment desired and the disorder indicated. The daily dosage of the compound of the invention may be in the range from 0.05 mg/kg to 100 mg/kg.

The compounds of formula (I) and pharmaceutically acceptable salts thereof may be used on their own but will generally be administered in the form of a pharmaceutical composition in which the formula (I) compound/salt (active ingredient) is in association with a pharmaceutically acceptable adjuvant, diluent or carrier. Conventional procedures for the selection and preparation of suitable pharmaceutical formulations are described in, for example, "Pharmaceuticals—The Science of Dosage Form Designs", M. E. Aulton, Churchill Livingstone, 1988.

Depending on the mode of administration, the pharmaceutical composition will preferably comprise from 0.05 to 99% w (percent by weight), more preferably from 0.05 to 80% w, still more preferably from 0.10 to 70% w, and even more preferably from 0.10 to 50% w, of active ingredient, all percentages by weight being based on total composition.

The present invention also provides a pharmaceutical composition comprising a compound of formula (I) or a pharmaceutically acceptable salt thereof as hereinbefore defined, in association with a pharmaceutically acceptable adjuvant, diluent or carrier.

The invention further provides a process for the preparation of a pharmaceutical composition of the invention which comprises mixing a compound of formula (I) or a pharmaceutically acceptable salt thereof as hereinbefore defined with a pharmaceutically acceptable adjuvant, diluent or carrier.

The pharmaceutical compositions may be administered topically (e.g. to the skin or to the lung and/or airways) in the form, e.g., of creams, solutions, suspensions, heptafluoroalkane (HFA) aerosols and dry powder formulations, for example, formulations in the inhaler device known as the Turbuhaler®; or systemically, e.g. by oral administration in the form of tablets, capsules, syrups, powders or granules; or by parenteral administration in the form of solutions or suspensions; or by subcutaneous administration; or by rectal administration in the form of suppositories; or transdermally.

Dry powder formulations and pressurized HFA aerosols of the compounds of the invention may be administered by oral or nasal inhalation. For inhalation, the compound is desirably finely divided. The finely divided compound preferably has a mass median diameter of less than 10 µm, and may be suspended in a propellant mixture with the assistance of a dispersant, such as a $C_8$-$C_{20}$ fatty acid or salt thereof, (for example, oleic acid), a bile salt, a phospholipid, an alkyl saccharide, a perfluorinated or polyethoxylated surfactant, or other pharmaceutically acceptable dispersant.

The compounds of the invention may also be administered by means of a dry powder inhaler. The inhaler may be a single or a multi dose inhaler, and may be a breath actuated dry powder inhaler.

One possibility is to mix the finely divided compound of the invention with a carrier substance, for example, a mono-, di- or polysaccharide, a sugar alcohol, or another polyol. Suitable carriers are sugars, for example, lactose, glucose, raffinose, melezitose, lactitol, maltitol, trehalose, sucrose, mannitol; and starch. Alternatively the finely divided compound may be coated by another substance. The powder mixture may also be dispensed into hard gelatine capsules, each containing the desired dose of the active compound.

Another possibility is to process the finely divided powder into spheres which break up during the inhalation procedure. This spheronized powder may be filled into the drug reservoir of a multidose inhaler, for example, that known as the Turbuhaler® in which a dosing unit meters the desired dose which is then inhaled by the patient. With this system the active ingredient, with or without a carrier substance, is delivered to the patient.

For oral administration the compound of the invention may be admixed with an adjuvant or a carrier, for example, lactose, saccharose, sorbitol, mannitol; a starch, for example, potato starch, corn starch or amylopectin; a cellulose derivative; a binder, for example, gelatine or polyvinylpyrrolidone; and/or a lubricant, for example, magnesium stearate, calcium stearate, polyethylene glycol, a wax, paraffin, and the like, and then compressed into tablets. If coated tablets are required, the cores, prepared as described above, may be coated with a concentrated sugar solution which may contain, for example, gum arabic, gelatine, talcum and titanium dioxide. Alternatively, the tablet may be coated with a suitable polymer dissolved in a readily volatile organic solvent.

For the preparation of soft gelatine capsules, the compound of the invention may be admixed with, for example, a vegetable oil or polyethylene glycol. Hard gelatine capsules may contain granules of the compound using either the above-mentioned excipients for tablets. Also liquid or semisolid formulations of the compound of the invention may be filled into hard gelatine capsules.

Liquid preparations for oral application may be in the form of syrups or suspensions, for example, solutions containing the compound of the invention, the balance being sugar and a mixture of ethanol, water, glycerol and propylene glycol. Optionally such liquid preparations may contain colouring agents, flavouring agents, saccharine and/or carboxymethylcellulose as a thickening agent or other excipients known to those skilled in art.

The compounds of the invention may also be administered in conjunction with other compounds used for the treatment of the above conditions.

Thus, the invention further relates to combination therapies wherein a compound of the invention, or a pharmaceutically acceptable salt thereof, or a pharmaceutical composition or formulation comprising a compound of the invention, is administered concurrently or sequentially or as a combined preparation with another therapeutic agent or agents, for the treatment of one or more of the conditions listed.

In particular, for the treatment of the inflammatory diseases such as (but not restricted to) rheumatoid arthritis, osteoarthritis, asthma, allergic rhinitis, chronic obstructive pulmonary disease (COPD), psoriasis, and inflammatory bowel disease, the compounds of the invention may be combined with agents listed below.

Non-steroidal anti-inflammatory agents (hereinafter NSAIDs) including non-selective cyclo-oxygenase COX-1/ COX-2 inhibitors whether applied topically or systemically (such as piroxicam, diclofenac, propionic acids such as naproxen, flurbiprofen, fenoprofen, ketoprofen and ibuprofen, fenamates such as mefenamic acid, indomethacin, sulindac, azapropazone, pyrazolones such as phenylbutazone, salicylates such as aspirin); selective COX-2 inhibitors (such as meloxicam, celecoxib, rofecoxib, valdecoxib, lumarocoxib, parecoxib and etoricoxib); cyclo-oxygenase inhibiting nitric oxide donors (CINODs); glucocorticosteroids (whether administered by topical, oral, intramuscular, intravenous, or intra-articular routes); methotrexate; leflunomide; hydroxychloroquine; d-penicillamine; auranofin or other parenteral or oral gold preparations; analgesics; diacerein; intra-articular therapies such as hyaluronic acid derivatives; and nutritional supplements such as glucosamine.

The present invention still further relates to the combination of a compound of the invention, or a pharmaceutically acceptable salt thereof, together with a cytokine or agonist or antagonist of cytokine function, (including agents which act on cytokine signalling pathways such as modulators of the SOCS system) including alpha-, beta-, and gamma-interferons; insulin-like growth factor type I (IGF-1); interleukins (IL) including IL1 to 23, and interleukin antagonists or inhibitors such as anakinra; tumour necrosis factor alpha (TNF-$\alpha$) inhibitors such as anti-TNF monoclonal antibodies (for example infliximab; adalimumab, and CDP-870) and TNF receptor antagonists including immunoglobulin molecules (such as etanercept) and low-molecular-weight agents such as pentoxyfylline. In addition the invention relates to a combination of a compound of the invention, or a pharmaceutically acceptable salt thereof, with a monoclonal antibody targeting B-Lymphocytes (such as CD20 (rituximab), MRA-aIL16R and T-Lymphocytes, CTLA4-Ig, HuMax I1-15).

The present invention still further relates to the combination of a compound of the invention, or a pharmaceutically acceptable salt thereof, with a modulator of chemokine receptor function such as an antagonist of CCR1, CCR2, CCR2A, CCR2B, CCR3, CCR4, CCR5, CCR6, CCR7, CCR8, CCR9, CCR10 and CCR11 (for the C—C family); CXCR1, CXCR2, CXCR3, CXCR4 and CXCR5 (for the C—X—C family) and $CX_3CR1$ for the C—$X_3$—C family.

The present invention further relates to the combination of a compound of the invention, or a pharmaceutically acceptable salt thereof, with an inhibitor of matrix metalloprotease (MMPs), i.e., the stromelysins, the collagenases, and the gelatinases, as well as aggrecanase; especially collagenase-1 (MMP-1), collagenase-2 (MMP-8), collagenase-3 (MMP-13), stromelysin-1 (IP-3), stromelysin-2 (MMP-10), and stromelysin-3 (MMP-11) and MMP-9 and MMP-12, including agents such as doxycycline.

The present invention still further relates to the combination of a compound of the invention, or a pharmaceutically acceptable salt thereof, and a leukotriene biosynthesis inhibitor, 5-lipoxygenase (5-LO) inhibitor or 5-lipoxygenase activating protein (FLAP) antagonist such as; zileuton; ABT-761; fenleuton; tepoxalin; Abbott-79175; Abbott-85761; a N-(5-substituted)-thiophene-2-alkylsulfonamide; 2,6-di-tert-butylphenolhydrazones; a methoxytetrahydropyrans such as Zeneca ZD-2138; the compound SB-210661; a pyridinyl-substituted 2-cyanonaphthalene compound such as L-739, 010; a 2-cyanoquinoline compound such as L-746,530; or an indole or quinoline compound such as MK-591, MK-886, and BAY x 1005.

The present invention further relates to the combination of a compound of the invention, or a pharmaceutically acceptable salt thereof, and a receptor antagonist for leukotrienes (LT) B4, LTC4, LTD4, and LTE4. selected from the group consisting of the phenothiazin-3-1s such as L-651,392; amidino compounds such as CGS-25019c; benzoxalamines such as ontazolast; benzenecarboximidamides such as BIIL 284/ 260; and compounds such as zafirlukast, ablukast, montelukast, pranlukast, verlukast (MK-679), RG-12525, Ro-245913, iralukast (CGP 45715A), and BAY x 7195.

The present invention still further relates to the combination of a compound of the invention, or a pharmaceutically acceptable salt thereof, and a phosphodiesterase (PDE) inhibitor such as a methylxanthanine including theophylline and aminophylline; a selective PDE isoenzyme inhibitor including a PDE4 inhibitor an inhibitor of the isoform PDE4D, or an inhibitor of PDE5.

The present invention further relates to the combination of a compound of the invention, or a pharmaceutically acceptable salt thereof, and a histamine type 1 receptor antagonist such as cetirizine, loratadine, desloratadine, fexofenadine, acrivastine, terfenadine, astemizole, azelastine, levocabastine, chlorpheniramine, promethazine, cyclizine, or mizolastine; applied orally, topically or parenterally.

The present invention still further relates to the combination of a compound of the invention, or a pharmaceutically acceptable salt thereof, and a proton pump inhibitor (such as omeprazole) or a gastroprotective histamine type 2 receptor antagonist.

The present invention further relates to the combination of a compound of the invention, or a pharmaceutically acceptable salt thereof, and an antagonist of the histamine type 4 receptor.

The present invention still further relates to the combination of a compound of the invention, or a pharmaceutically acceptable salt thereof, and an alpha-1/alpha-2 adrenoceptor agonist vasoconstrictor sympathomimetic agent, such as propylhexedrine, phenylephrine, phenylpropanolamine, ephedrine, pseudoephedrine, naphazoline hydrochloride, oxymetazoline hydrochloride, tetrahydrozoline hydrochloride, xylometazoline hydrochloride, tramazoline hydrochloride or ethylnorepinephrine hydrochloride.

The present invention further relates to the combination of a compound of the invention, or a pharmaceutically acceptable salt thereof, and an anticholinergic agents including muscarinic receptor (M1, M2, and M3) antagonist such as atropine, hyoscine, glycopyrrrolate, ipratropium bromide, tiotropium bromide, oxitropiuni bromide, pirenzepine or telenzepine.

The present invention still further relates to the combination of a compound of the invention, or a pharmaceutically acceptable salt thereof, and a beta-adrenoceptor agonist (including beta receptor subtypes 1-4) such as isoprenaline, salbutamol, formoterol, salmeterol, terbutaline, orciprenaline, bitolterol mesylate, or pirbuterol, or a chiral enantiomer thereof.

The present invention further relates to the combination of a compound of the invention, or a pharmaceutically acceptable salt thereof, and a chromone, such as sodium cromoglycate or nedocromil sodium.

The present invention still further relates to the combination of a compound of the invention, or a pharmaceutically acceptable salt thereof, with a glucocorticoid, such as flunisolide, triamcinolone acetonide, beclomethasone dipropionate, budesonide, fluticasone propionate, ciclesonide or mometasone furoate.

The present invention further relates to the combination of a compound of the invention, or a pharmaceutically acceptable salt thereof, with an agent that modulates a nuclear hormone receptor such as PPARs.

The present invention still further relates to the combination of a compound of the invention, or a pharmaceutically acceptable salt thereof, together with an immunoglobulin (Ig) or Ig preparation or an antagonist or antibody modulating Ig function such as anti-IgE (for example omalizumab).

The present invention further relates to the combination of a compound of the invention, or a pharmaceutically acceptable salt thereof, and another systemic or topically-applied anti-inflammatory agent, such as thalidomide or a derivative thereof, a retinoid, dithranol or calcipotriol.

The present invention still further relates to the combination of a compound of the invention, or a pharmaceutically acceptable salt thereof, and combinations of aminosalicylates and sulfapyridine such as sulfasalazine, mesalazine, balsalazide, and olsalazine; and immunomodulatory agents such as the thiopurines, and corticosteroids such as budesonide.

The present invention further relates to the combination of a compound of the invention, or a pharmaceutically acceptable salt thereof, together with an antibacterial agent such as a penicillin derivative, a tetracycline, a macrolide, a beta-lactam, a fluoroquinolone, metronidazole, an inhaled aminoglycoside; an antiviral agent including acyclovir, famciclovir, valaciclovir, ganciclovir, cidofovir, amantadine, rimantadine, ribavirin, zanamavir and oseltamavir; a protease inhibitor such as indinavir, nelfinavir, ritonavir, and saquinavir; a nucleoside reverse transcriptase inhibitor such as didanosine, lamivudine, stavudine, zalcitabine or zidovudine; or a non-nucleoside reverse transcriptase inhibitor such as nevirapine or efavirenz.

The present invention still further relates to the combination of a compound of the invention, or a pharmaceutically acceptable salt thereof, and a cardiovascular agent such as a calcium channel blocker, a beta-adrenoceptor blocker, an angiotensin-converting enzyme (ACE) inhibitor, an angiotensin-2 receptor antagonist; a lipid lowering agent such as a statin or a fibrate; a modulator of blood cell morphology such as pentoxyfylline; thrombolytic, or an anticoagulant such as a platelet aggregation inhibitor.

The present invention further relates to the combination of a compound of the invention, or a pharmaceutically acceptable salt thereof, and a CNS agent such as an antidepressant (such as sertraline), an anti-Parkinsonian drug (such as deprenyl, L-dopa, ropinirole, pramipexole, a MAOB inhibitor such as selegine and rasagiline, a comP inhibitor such as tasmar, an A-2 inhibitor, a dopamine reuptake inhibitor, an NMDA antagonist, a nicotine agonist, a dopamine agonist or an inhibitor of neuronal nitric oxide synthase), or an anti-Alzheimer's drug such as donepezil, rivastigmine, tacrine, a COX-2 inhibitor, propentofylline or metrifonate.

The present invention still further relates to the combination of a compound of the invention, or a pharmaceutically acceptable salt thereof, and an agent for the treatment of acute or chronic pain, such as a centrally or peripherally-acting analgesic (for example an opioid or derivative thereof), carbamazepine, phenyloin, sodium valproate, amitryptiline or other anti-depressant agent-s, paracetamol, or a non-steroidal anti-inflammatory agent.

The present invention further relates to the combination of a compound of the invention, or a pharmaceutically acceptable salt thereof, together with a parenterally or topically-applied (including inhaled) local anaesthetic agent such as lignocaine or a derivative thereof.

A compound of the present invention, or a pharmaceutically acceptable salt thereof, can also be used in combination with an anti-osteoporosis agent including a hormonal agent such as raloxifene, or a biphosphonate such as alendronate.

The present invention still further relates to the combination of a compound of the invention, or a pharmaceutically acceptable salt thereof, together with a: (i) tryptase inhibitor; (ii) platelet activating factor (PAF) antagonist; (iii) interleukin converting enzyme (ICE) inhibitor; (iv) IMPDH inhibitor; (v) adhesion molecule inhibitors including VLA-4 antagonist; (vi) cathepsin; (vii) kinase inhibitor such as an inhibitor of tyrosine kinase (such as Btk, Itk, Jak3 or MAP, for example Gefitinib or Imatinib mesylate), a serine/threonine kinase (such as an inhibitor of a MAP kinase such as p38, JNK, protein kinase A, B or C, or IKK), or a kinase involved in cell cycle regulation (such as a cylin dependent kinase); (viii) glucose-6 phosphate dehydrogenase inhibitor; (ix) kinin-B.sub1.- or B.sub2.-receptor antagonist; (x) anti-gout agent, for example colchicine; (xi) xanthine oxidase inhibitor, for example allopurinol; (xii) uricosuric agent, for example probenecid, sulfinpyrazone or benzbromarone; (xiii) growth hormone secretagogue; (xiv) transforming growth factor (TGFβ); (xv) platelet-derived growth factor (PDGF); (xvi) fibroblast growth factor for example basic fibroblast growth factor (bFGF); (xvii) granulocyte macrophage colony stimulating factor (GM-CSF); (xviii) capsaicin cream; (xix) tachykinin NK.sub1. or NK.sub3. receptor antagonist such as NKP-608C, SB-233412 (talnetant) or D-4418; (xx) elastase inhibitor such as UT-77 or ZD-0892; (xxi) TNF-alpha converting enzyme inhibitor (TACE); (xxii) induced nitric oxide synthase (iNOS) inhibitor; (xxiii) chemoattractant receptor-homologous molecule expressed on TH2 cells, (such as a CRTH2 antagonist); (xxiv) inhibitor of P38; (xxv) agent modulating the function of Toll-like receptors (TLR), (xxvi) agent modulating the activity of purinergic receptors such as P2X7; or (xxvii) inhibitor of transcription factor activation such as NFkB, API, or STATS.

A compound of the invention, or a pharmaceutically acceptable salt thereof, can also be used in combination with an existing therapeutic agent for the treatment of cancer, for example suitable agents include:

(i) an antiproliferative/antineoplastic drug or a combination thereof, as used in medical oncology, such as an alkylating agent (for example cis-platin, carboplatin, cyclophosphamide, nitrogen mustard, melphalan, chlorambucil, busulphan or a nitrosourea); an antimetabolite (for example an antifolate such as a fluoropyrimidine like 5-fluorouracil or tegafur, raltitrexed, methotrexate, cytosine arabinoside, hydroxyurea, gemcitabine or paclitaxel); an antitumour antibiotic (for example an anthracycline such as adriamycin, bleomycin, doxorubicin, daunomycin, epirubicin, idarubicin, mitomycin-C, dactinomycin or mithramycin); an antimitotic agent (for example a vinca alkaloid such as vincristine, vinblastine, vindesine or vinorelbine, or a taxoid such as taxol or taxotere); or a topoisomerase inhibitor (for example an epipodophyllotoxin such as etoposide, teniposide, amsacrine, topotecan or a camptothecin);

(ii) a cytostatic agent such as an antioestrogen (for example tamoxifen, toremifene, raloxifene, droloxifene or iodoxyfene), an oestrogen receptor down regulator (for example fulvestrant), an antiandrogen (for example bicalutamide, flutamide, nilutamide or cyproterone acetate), a LHRH antagonist or LHRH agonist (for example goserelin, leuprorelin or buserelin), a progestogen (for example megestrol acetate), an aromatase inhibitor (for example as anastrozole, letrozole, vorazole or exemestane) or an inhibitor of 5α-reductase such as fmasteride;

(iii) an agent which inhibits cancer cell invasion (for example a metalloproteinase inhibitor like marimastat or an inhibitor of urokinase plasminogen activator receptor function);

(iv) an inhibitor of growth factor function, for example: a growth factor antibody (for example the anti-erbb2 antibody trastuzumab, or the anti-erbb1 antibody cetuximab [C225]), a farnesyl transferase inhibitor, a tyrosine kinase inhibitor or a serine/threonine kinase inhibitor, an inhibitor of the epidermal growth factor family (for example an EGFR family tyrosine kinase inhibitor such as N-(3-chloro-4-fluorophenyl)-7-methoxy-6-(3-morpholinopropoxy)quinazolin-4-amine (gefitinib, AZD1839), N-(3-ethynylphenyl)-6,7-bis(2-methoxyethoxy)quinazolin-4-amine (erlotinib, OSI-774) or 6-acrylamido-N-(3-chloro-4-fluorophenyl)-7-(3-morpholinopropoxy)quinazolin-4-amine (CI 1033)), an inhibitor of the platelet-derived growth factor family, or an inhibitor of the hepatocyte growth factor family;

(v) an antiangiogenic agent such as one which inhibits the effects of vascular endothelial growth factor (for example the anti-vascular endothelial cell growth factor antibody bevacizumab, a compound disclosed in WO 97/22596, WO 97/30035, WO 97/32856 or WO 98/13354), or a compound that works by another mechanism (for example linomide, an inhibitor of integrin αvβ3 function or an angiostatin);

(vi) a vascular damaging agent such as combretastatin A4, or a compound disclosed in WO 99/02166, WO 00/40529, WO 00/41669, WO 01/92224, WO 02/04434 or WO 02/08213;

(vii) an agent used in antisense therapy, for example one directed to one of the targets listed above, such as ISIS 2503, an anti-ras antisense;

(viii) an agent used in a gene therapy approach, for example approaches to replace aberrant genes such as aberrant p53 or aberrant BRCA1 or BRCA2, GDEPT (gene-directed enzyme pro-drug therapy) approaches such as those using cytosine deaminase, thymidine kinase or a bacterial nitroreductase enzyme and approaches to increase patient tolerance to chemotherapy or radiotherapy such as multi-drug resistance gene therapy; or (ix) an agent used in an immunotherapeutic approach, for example ex-vivo and in-vivo approaches to increase the immunogenicity of patient tumour cells, such as transfection with cytokines such as interleukin 2, interleukin 4 or granulocyte-macrophage colony stimulating factor, approaches to decrease T-cell anergy, approaches using transfected immune cells such as cytokine-transfected dendritic cells, approaches using cytokine-transfected tumour cell lines and approaches using anti-idiotypic antibodies.

In particular the compounds of the invention may be administered in conjunction with a second active ingredient which is selected from:

a) a PDE4 inhibitor including an inhibitor of the isoform PDE4D;
b) a β-adrenoceptor agonist such as metaproterenol, isoproterenol, isoprenaline, albuterol, salbutamol, formoterol, salmeterol, terbutaline, orciprenaline, bitolterol mesylate, pirbuterol or indacaterol;
c) a muscarinic receptor antagonist (for example a M1, M2 or M3 antagonist, such as a selective M3 antagonist) such as ipratropium bromide, tiotropium bromide, oxitropium bromide, pirenzepine or telenzepine;
d) a modulator of chemokine receptor function (such as a CCR1 or CCR8 receptor antagonist);
e) an inhibitor of kinase function;
f) a non-steroidal glucocorticoid receptor agonist;
g) a steroidal glucocorticoid receptor agonist; and
h) a protease inhibitor (such as a MMP12 or MMP9 inhibitor);

The present invention will now be further explained by reference to the following illustrative examples.

General Methods $^1$H NMR and $^{13}$C NMR spectra were recorded on a Varian Inova 400 MHz or a Varian Mercury-VX 300 MHz instrument. The central peaks of chloroform-d ($\delta_H$ 7.27 ppm), dimethylsulfoxide-d$_6$ ($\delta_H$ 2.50 ppm), acetonitrile-d$_3$ ($\delta_H$ 1.95 ppm) or methanol-d$_4$ ($\delta_H$ 3.31 ppm) were used as internal references. Column chromatography was carried out using silica gel (0.040-0.063 mm, Merck). Unless stated otherwise, starting materials were commercially available. All solvents and commercial reagents were of laboratory grade and were used as received.

The following method was used for LC/MS analysis: Instrument Agilent 1100; Column Waters Symmetry 2.1×30 mm; Mass APCI; Flow rate 0.7 ml/min; Wavelength 254 nm; Solvent A: water+0.1% TFA; Solvent B: acetonitrile+0.1% TFA; Gradient 15-95%/B 8 min, 95% B 1 min.

Analytical chromatography was run on a Symmetry C$_{18}$-column, 2.1×30 mm with 3.5 μm particle size, with acetonitrile/water/0.1% trifluoroacetic acid as mobile phase in a gradient from 5% to 95% acetonitrile over 8 minutes at a flow of 0.7 ml/min.

The abbreviations or terms used in the examples have the following meanings:

HATU: O-(7-Azabenzotriazol-1-yl)-N,N,N',N'-tetramethyluronium hexafluorophosphate
HOAT: 1-Hydroxy-7-azabenzotriazole
NMP: 1-N-Methyl-2-pyrrolidinone
THF: Tetrahydrofuran
DCM: Dichloromethane
DIEA: N,N-Diisopropylethylamine
DME: 1,2-Dimethoxyethane
EtOAc: Ethyl acetate
DMSO: Dimethyl sulphoxide
SM: Starting material
Ex: Example
Aq: Aqueous
RT: Room temperature

EXAMPLE 1

5-[1-(4-Cyanophenyl)-1H-pyrazol-5-yl]-N,6-dimethyl-2-oxo-1-[3-(trifluoromethyl)phenyl]-1,2-dihydropyridine-3-carboxamide Argon was bubbled through 5-iodo-N,6-dimethyl-2-oxo-1-[3-(trifluoromethyl)phenyl]-1,2-dihydropyridine-3-carboxamide (SM2, 200 mg, 0.46 mmol) and [1-(4-cyanophenyl)-1H-pyrazol-5-yl]boronic acid (SM3, 150 mg, 0.70 mmol) in DME (10 ml) and 2M Na$_2$CO$_3$ (5 ml) for 10 min. Palladium-tri-tert-butylphosphine (25 mg, 0.049 mmol) was added and the mixture was stirred under argon at 82° C. for 2 h. More SM3 (150 mg, 0.70 mmol) and palladium-tri-tert-butylphosphine (10 mg, 0.019 mmol) were added and the mixture was stirred for a further 2 h under the same conditions. The reaction mixture was then was cooled to RT, diluted with ethyl acetate (150 ml) and washed with brine (3×100 ml). The organic phase was dried (Na$_2$SO$_4$), filtered and evaporated. The residue was purified by HPLC on a Kromasil C-18 column using a gradient of acetonitrile/water. Freeze-drying of the mixture afforded the title compound (80 mg).

$^1$H NMR (399.99 MHz, DMSO-D$_6$) δ 9.18 (q, J=4.78 Hz, 1H), 8.05 (s, 1H), 7.96-7.64 (m, 9H), 6.72 (d, J=1.76 Hz, 1H), 2.76 (d, J=4.77 Hz, 3H), 1.76 (s, 3H);

APCI-MS m/z: 478.3 [MH$^+$].

EXAMPLE 2

The following compound was synthesised in an analogous manner to Example 1.

| Ex | Compound | ¹H NMR | m/z | SM |
|---|---|---|---|---|
| 2 | 5-[1-(4-Cyanophenyl)-1H-pyrazol-5-yl]-6-methyl-N-[4-(methylsulfonyl)benzyl]-2-oxo-1-[3-(trifluoromethyl)phenyl]-1,2-dihydropyridine-3-carboxamide | 9.81 (t, J = 6.01 Hz, 1H), 8.10 (s, 1H), 7.96-7.70 (mm, 9H), 7.67 (d, J = 8.67 Hz, 2H), 7.52 (d, J = 8.31 Hz, 2H), 6.73 (d, J = 2.77 Hz, 1H), 4.55 (d, J = 6.01 Hz, 2H), 3.17 (s, 3H), 1.76 (s, 3H). | 632.2 | SM1 SM3 |

EXAMPLE 3

5-[2-Amino-5-(4-chlorophenyl)-1,3-thiazol-4-yl]-N,6-dimethyl-2-oxo-1-[3-(trifluoromethyl)-phenyl]-1,2-dihydropyridine-3-carboxamide Thiourea (8.5 mg, 0.11 mmol) was added to 5-[bromo(4-chlorophenyl)acetyl]-N,6-dimethyl-2-oxo-1-[3-(trifluoromethyl)phenyl]-1,2-dihydropyridine-3-carboxamide (SM4, mg, 55 mmol) in acetonitrile (1 ml) and the mixture was heated in a microwave oven to 120° C. for 10 min. The crude product was purified on an Xterra C8 column using a gradient of acetonitrile/water. Freeze drying of the mixture afforded the title compound (10 mg, 35%).

¹H NMR (400 MHz, DMSO-D$_6$) δ 9.27 (d, J=4.8 Hz, 1H), 8.27 (s, 1H), 7.88 (d, J=8.0 Hz, 2H), 7.81 (t, J=7.6 Hz, 3H), 7.67 (d, J=7.8 Hz, 1H), 7.37 (d, J=8.5 Hz, 4H), 7.32 (s, 3H), 7.25 (d, J=8.5 Hz, 2H), 2.77 (d, J=4.6 Hz, 3H), 1.67 (s, 3H); APCI-MS m/z: 519.0 [MH$^+$].

EXAMPLES 4 AND 5

The following compounds were synthesised in an analogous manner to Example 3.

| Ex | Compound | ¹H NMR | m/z | SM |
|---|---|---|---|---|
| 4 | 5-[4-(4-Chlorophenyl)-1,3-oxazol-5-yl]-N,6-dimethyl-2-oxo-1-[3-(trifluoromethyl)phenyl]-1,2-dihydropyridine-3-carboxamide | ¹H NMR (400 MHz, CDCl$_3$) δ 9.32 (s, 1H), 8.61 (s, 1H), 8.02 (d, J = 6.2 Hz, 1H), 7.83 (d, J = 7.6 Hz, 2H), 7.76 (t, J = 7.8 Hz, 2H), 7.55 (s, 1H), 7.48 (d, J = 8.5 Hz, 3H), 7.39 (d, J = 8.5 Hz, 2H), 2.94 (d, J = 5.0 Hz, 3H), 1.99 (s, 3H). | 488.0 | SM4 |
| 5 | 5-[2-Amino-5-(4-cyanophenyl)-1,3-thiazol-4-yl]-N,6-dimethyl-2-oxo-1-[3-(trifluoromethyl)phenyl]-1,2-dihydropyridine-3-carboxamide | ¹H NMR (399.99 MHz, DMSO-D$_6$) δ 9.26 (d, J = 4.8 Hz, 1H), 8.27 (s, 1H), 7.85 (m, 3H), 7.75 (d, 2H), 7.69 (d, J = 8.1 Hz, 1H), 7.41 (s, 2H), 2.78 (d, J = 4.8 Hz, 3H), 1.69 (s, 3H). | 510.0 | |

EXAMPLE 6

The following compound was synthesised in an analogous manner to Example 1.

1-(3-Chloro-4-fluorophenyl)-5-[1-(4-cyanophenyl)-1H-pyrazol-5-yl]-N,6-dimethyl-2-oxo-1,2-dihydro-pyridine-3-carboxamide $^1$H NMR (300 MHz, DMSO-D$_6$) δ 9.18 (q, 1H), 8.02 (s, 1H), 7.96-7.90 (m, 3H), 7.78 (dd, 1H), 7.71-7.60 (m, 3H), 7.43 (m, 1H), 6.70 (d, 1H), 2.76 (d, 3H), 1.81 (s, 3H);
APCI-MS m/z: 462 [MH$^+$].

EXAMPLE 7

5-[2-(4-Chloro-phenyl)-2H-pyrazol-3-yl]-6-methyl-2-oxo-1-(3-trifluoromethyl-phenyl)-1,2-dihydro-pyridine-3-carboxylic acid methylamide a) 1-(4-Chloro-phenyl)-5-tributylstannanyl-1H-pyrazole 2,2,6,6-Tetramethylpiperidine (TMP, 0.25 g, 1.78 mmol) was dissolved in dry THF (10 ml) in a flask with a magnetic stirrer bar. The flask was flushed with argon and kept under an inert atmosphere. The mixture was cooled to −78° C., and n-BuLi (1.1 ml, 1.6M, 1.78 mmol) was added dropwise during 1 minute. The mixture was stirred for 5 minutes at this temperature, before adding a solution of 1-(4-chloro-phenyl)-1H-pyrazole (0.21 g, 1.1 mmol) in dry THF (2 ml). The solution was added dropwise over 2 minutes, and the obtained solution was stirred at this temperature for 20 minutes, before adding Bu$_3$SnCl (0.36 g, 1.1 mmol) over 1 minute. The solution was allowed to slowly warm to RT and was then quenched with MeOH (1 ml). The residual mixture was partitioned between EtOAc and water, and the organic phase was dried and concentrated. Purification on silica afforded 0.2 g (40%) of an oil.

$^1$H NMR (400 MHz, DMSO-D$_6$) δ 7.77 (d, J=1.8 Hz, 1H), 7.62 (d, J=9.0 Hz, 2H), 7.42 (d, J=9.0 Hz, 2H), 6.54 (d, J=1.8 Hz, 1H), 1.50-0.67 (m, 27H).
APCI-MS m/z: 468 [MH$^+$].

b) 5-[2-(4-Chloro-phenyl)-2H-pyrazol-3-yl]-6-methyl-2-oxo-1-(3-trifluoromethyl-phenyl)-1,2-dihydro-pyridine-3-carboxylic acid methylamide 1-(4-Chloro-phenyl)-5-tributylstannanyl-1H-pyrazole (0.107 g, 0.22 mmol), 5-iodo-6-methyl-2-oxo-1-(3-trifluoromethyl-phenyl)-1,2-dihydro-pyridine-3-carboxylic acid methylamide (0.05 g, 0.11 mmol), Pd(PBu$^t_3$)$_2$ (10 mg) and DME (2 ml) were placed in a tube for microwave synthesis. The mixture was degassed with argon and heated in a synthesis microwave heater (CEM) at 100° C. (max 150 W) for 10 minutes. The solvent was removed in vacuo giving a crude product which was purified on silica and then further purified on preparative HPLC. The pure fractions were freeze-dried giving 10 mg (17%) of the title compound.

$^1$H NMR (400 MHz, DMSO-D$_6$) δ 9.23-9.12 (m, 1H), 8.03 (s, 1H), 7.91 (d, J=8.0 Hz, 1H), 7.87-7.80 (m, 3H), 7.69 (d, J=8.0 Hz, 1H), 7.53 (d, J=8.8 Hz, 2H), 7.45 (d, J=8.8 Hz, 2H), 6.66 (d, J=1.8 Hz, 1H), 2.75 (d, J=4.8 Hz, 3H), 1.77 (s, 3H).
APCI-MS m/z: 487.0 [MH$^+$].

EXAMPLE 8

5-[2-(4-Fluoro-phenyl)-2H-pyrazol-3-yl]-6-methyl-2-oxo-1-(3-trifluoromethyl-phenyl)-1,2-dihydro-pyridine-3-carboxylic acid methylamide a) 1-(4-Fluoro-phenyl)-5-tributylstannanyl-1H-pyrazole

The compound was prepared by an analogous procedure to that described in Example 7(a).
APCI-MS m/z: 452 [MH$^+$].

b) 5-[2-(4-Fluoro-phenyl-2H-pyrazol-3-yl]-6-methyl-2-oxo-1-(3-trifluoromethyl-phenyl)-1,2-dihydro-pyridine-3-carboxylic acid methylamide 1-(4-Fluoro-phenyl)-5-tributylstannanyl-1H-pyrazole (0.100 g, 0.22 mmol), 5-iodo-6-methyl-2-oxo-1-(3-trifluoromethyl-phenyl)-1,2-dihydro-pyridine-3-carboxylic acid methylamide (0.05 g, 0.11 mmol), Pd(PBu$_3$)$_2$ (10 mg) and DME (2 ml) were placed in a tube for microwave synthesis. The mixture was degassed with argon and heated in a synthesis microwave heater (CEM) at 100° C. (max 150 W) for 10 minutes. The solvent was removed in vacuo giving a crude product which was purified on silica and then further purified on preparative HPLC. The pure fractions were freeze-dried giving 10 mg (17%) of the title compound.

$^1$H NMR (400 MHz, DMSO-D$_6$) δ 9.22-9.13 (m, 1H), 8.04 (s, 1H), 7.91 (d, J=7.7 Hz, 1H), 7.86-7.80 (m, 3H), 7.67 (d, J=7.7 Hz, 1H), 7.49-7.42 (m, 2H), 7.30 (t, J=8.8 Hz, 2H), 6.65 (d, J=1.8 Hz, 1H), 2.75 (d, J=4.8 Hz, 3H), 1.76 (s, 3H).
APCI-MS m/z: 471.0 [MH$^+$].

EXAMPLE 9

5-[3-(4-Cyano-phenyl)-3H-[1,2,3]triazol-4-yl]-6-methyl-2-oxo-1-(3-trifluoromethyl-phenyl)-1,2-dihydro-pyridine-3-carboxylic acid methylamide a) 4-[1,2,3]-Triazol-1-yl-benzonitrile

4-Fluorobenzonitrile (0.847 g, 7 mmol), 1H-[1,2,3]triazole (0.483 g, 7 mmol), Cs$_2$CO$_3$ (2.27 g, 7 mmol) and DMF (8 ml) and a magnetic stirrer were placed in a vial. The mixture was heated with stirring for 3 h at 80° C. Extractive work-up (EtOAc/H$_2$O) and subsequent drying (Na$_2$SO$_4$) gave a crude product which was purified on silica giving 0.55 g (46%) of the title compound.

$^1$H NMR (400 MHz, DMSO-D$_6$) δ 9.00 (d, J=1.2 Hz, 1H), 8.18 (d, J=8.8 Hz, 2H), 8.11 (d, J=8.8 Hz, 2H), 8.05 (d, J=1.2 Hz, 1H).

b) 4-(5-Tributylstannanyl-[1,2,3]triazol-1-yl)-benzonitrile

4-[1,2,3]Triazol-1-yl-benzonitrile (0.105 g, 0.6 mmol) and dry THF (6 ml) and a magnetic stirrer were placed in a flask. The flask was flushed with argon and kept under an inert atmosphere and cooled to −78° C. At this temperature, tert-BuLi (0.36 ml, 1.7M, 0.6 mmol) was added dropwise during 1 to 2 minutes. The mixture was stirred at this temperature for 15 minutes and Bu$_3$SnCl (0.19 g, 0.6 mmol) was added during 1 minute, and the mixture was then allowed to slowly reach RT. The crude mixture was directly purified on silica (heptane:EtOAc 4:1) giving 0.12 g (43%) of the title stannane.
APCI-MS m/z: 460 [MH+].

c) 5-[3-(4-Cyano-phenyl)-3H-[1,2,3]triazol-4-yl]-6-methyl-2-oxo-1-(3-trifluoromethyl-phenyl)-1,2-dihydro-pyridine-3-carboxylic acid methylamide 4-(5-Tributylstannanyl-[1,2,3]triazol-1-yl)-benzonitrile (0.107 g, 0.22 mmol), 5-iodo-6-methyl-2-oxo-1-(3-trifluoromethyl-phenyl)-1,2-dihydro-pyridine-3-carboxylic acid methylamide (0.05 g, 0.11 mmol), Pd(PBu$^t{}_3$)$_2$ (10 mg) and DME (2 ml) were placed in a tube for microwave synthesis. The mixture was degassed with argon and heated in a synthesis microwave heater (CEM) at 100° C. (max 150 W) for 10 minutes. The solvent was removed in vacuo giving a crude product which was purified on silica and then further purified on preparative HPLC. The pure fractions were freeze-dried giving 20 mg (40%) of the title compound.
$^1$H NMR (400 MHz, DMSO-D$_6$) δ 9.17-9.09 (m, 1H), 8.12 (s, 1H), 8.09-8.02 (m, 3H), 7.92 (d, J=7.8 Hz, 1H), 7.88-7.82 (m, 2H), 7.80 (d, J=8.6 Hz, 2H), 7.80 (d, J=8.0 Hz, 1H), 2.74 (d, J=4.8 Hz, 3H), 1.80 (s, 3H).
APCI-MS m/z: 479.0 [MH+].

EXAMPLE 10

5-[1-(4-Cyanophenyl)-1H-1,2,4-triazol-5-yl]-N6-dimethyl-2-oxo-1-[3-(trifluoromethyl)phenyl]-1,2-dihydropyridine-3-carboxamide 5-Iodo-N,6-dimethyl-2-oxo-1-[3-(trifluoromethyl)phenyl]-1,2-dihydropyridine-3-carboxamide (SM2, 0.051 g, 0.117 mmol), 4-(1H-1,2,4-triazol-1-yl)benzonitrile (0.020 g, 0.117 mmol), copper(I) iodide (0.044 g, 0.234 mmol), cesium fluoride (0.036 g, 0.234 mmol) and NMP (0.5 ml) were placed in a vial. Argon was bubbled through the stirred mixture for 10 min. Palladium(II) acetate (0.002 g, 0.0089 mmol) was added and the vial was sealed and stirred at 140° C. for 6 h. Two more experiments were run the same way and the three reaction mixtures were combined and purified by preparative HPLC to give 0.003 g (2%) of the title compound.
$^1$H NMR (400 MHz, DMSO-D$_6$) δ 9.16-9.09 (m, 1H), 8.42 (s, 1H), 8.16 (s, 1H), 8.01 (d, J=8.7 Hz, 2H), 7.92 (d, J=8.9 Hz, 2H), 7.84 (t, J=7.7 Hz, 1H), 7.80-7.74 (m, 3H), 2.75 (d, J=4.7 Hz, 3H), 1.85 (s, 3H).
APCI-MS m/z: 479.0 [MH+].

Preparation of Starting Materials

The starting materials for the examples above are either commercially available or are readily prepared by standard methods from known materials. For example, the following reactions are illustrations, but not a limitation, of the preparation of some of the starting materials.

Starting Material SM1

5-Iodo-6-methyl-N-[4-(methylsulfonyl)benzyl]-2-oxo-1-[3-(trifluoromethyl)phenyl]-1,2-dihydropyridine-3-carboxamide To an ice-cooled solution of 3-(trifluoromethyl)aniline (64.5 g, 0.40 mol) and triethylamine (60 ml) in acetone (700 ml) was added dropwise, ethyl 3-chloro-3-oxopropanoate (63.6 g, 0.42 mol) in acetone (50 ml). After the addition was complete (approx. 30 minutes), stirring was continued at RT overnight. The solvents were removed and water (1200 ml) was added. The resulting precipitate was filtered off, thoroughly washed twice with water and then dried to afford ethyl 3-oxo-3-{[3-(trifluoromethyl)phenyl]amino}propanoate as a yellow powder (109 g, 99%).
$^1$H NMR (399.99 MHz, CDCl$_3$): δ 9.52 (1H, s); 7.87 (1H, s); 7.78 (1H, d); 7.46 (1H, t); 7.39 (1H, d); 4.29 (2H, q); 3.50 (2H, s); 1.35 (3H, t).
APCI-MS m/z: 276.1 [MH+].

To a solution of ethyl 3-oxo-3-{[3-(trifluoromethyl)phenyl]amino}propanoate (19.2 g, 70 mmol) and sodium methoxide (7.6 g, 140 mmol) in EtOH (250 ml) was added 4-methoxybut-3-en-2-one (90%) (7.72 g, 77 mmol). After the addition, the reaction mixture was refluxed for 2 h and then cooled. Water (50 ml) and 2M NaOH were added and the mixture was stirred at RT overnight. The organic solvents were removed and the reaction mixture was extracted (washed) with EtOAc. The water phases were acidified with hydrochloric acid to pH 3 to 4, an orange coloured precipitate appeared and was filtered off, washed with water and dried. Recrystallisation twice from heptane/EtOAc (4:1) afforded 6-methyl-2-oxo-1-[3-(trifluoromethyl)phenyl]-1,2-dihydropyridine-3-carboxylic acid (12 g, 58%) as a white powder.
$^1$H NMR (399.99 MHz, CDCl$_3$): δ 13.68 (1H, s); 8.54 (1H, d); 7.86 (1H, d); 7.79 (1H, t); 7.55 (1H, brs); 7.48 (1H, d); 6.58 (1H, d); 2.16 (3H, s);
APCI-MS m/z: 298.1 [MH+].

A mixture of 6-methyl-2-oxo-1-[3-(trifluoromethyl)phenyl]-1,2-dihydropyridine-3-carboxylic acid (7.43 g, 25 mmol), HATU (10.5 g, 27.5 mmol), HOAT (3.75 g, 27.5 mmol) and DIEA (14.2 ml, 82.5 mmol) in NMP (65 ml) was reacted for 1 h, then 4-methylsulphonylbenzyl amine hydrochloride (5.8 g, 26 mmol) was added. After 1 h, the reaction mixture was slowly poured into stirred ice water (1 L). A powder was formed and the water mixture was acidified to pH 3 with 0.5M citric acid, and stirring was continued for 1 h. The precipitate was filtered off, washed with water and dried in vacuum overnight. Recrystallisation from EtOAc gave 6-methyl-N-[4-(methylsulfonyl)benzyl]-2-oxo-1-[3-(trifluoromethyl)phenyl]-1,2-dihydropyridine-3-carboxamide (8.1 g, 70%).
$^1$H NMR (399.99 MHz, CDCl$_3$): δ 10.00 (1H, brt); 8.60 (1H, d); 7.88 (2H, d); 7.83 (1H, d); 7.76 (1H, t); 7.53 (3H, m); 7.46 (1H, d); 6.49 (1H, d); 4.68 (2H, m); 3.03 (3H, s); 2.10 (3H, s);
APCI-MS m/z: 465.1 [MH+].

To a solution of 6-methyl-N-[4-(methylsulfonyl)benzyl]-2-oxo-1-[3-(trifluoromethyl)phenyl]-1,2-dihydropyridine-3-carboxamide (200 mg, 0.43 mmol) in MeCN (1.5 ml) at RT and under argon, was added trifluoromethanesulfonic acid (1 ml) followed by N-iodosuccinimide (97 mg, 0.43 mmol). After 45 min, the reaction mixture was diluted with DCM, washed with aqueous NaHCO$_3$, with aqueous NaS$_2$O$_4$ and water, dried (Na$_2$SO$_4$), and evaporated to give the title compound SM1 (200 mg).
$^1$H NMR (399.99 MHz, CDCl$_3$): δ 9.85 (1H, brt); 8.90 (1H, d); 7.88 (2H, d); 7.76 (2H, m); 7.50 (2H, d); 7.48 (1H, s); 7.40 (1H, d); 4.65 (2H, m); 3.03 (3H, s); 2.32 (3H, s);
APCI-MS m/z: 591.0 [MH+].

Starting Material SM2

SM2, 5-iodo-N,6-dimethyl-2-oxo-1-[3-(trifluoromethyl)phenyl]-1,2-dihydropyridine-3-carboxamide, was synthesised in an analogous manner to SM1.

Starting Material SM3

[1-(4-Cyanophenyl)-1H-pyrazol-5-yl]boronic acid 4-(1H-Pyrazol-1-yl)benzonitrile (Eur. J. Org. Chem. 2004, 695-709) (1.5 g, 8.87 mmol) in dry THF (50 ml) under argon was stirred at −78° C. whilst lithium diisopropylamide (1.8M solution in THF/hexane/ethyl benzene; 5.2 ml, 9.32 mmol) was added dropwise during 20 min. Stirring and cooling were continued for 1 h, triisopropyl borate (8 ml, 34.5 mmol) was added dropwise during 30 min and then the temperature was allowed to rise overnight to RT. The pH of the reaction mixture was adjusted to 5 with 1M HCl and the mixture was then concentrated to a minimum volume and extracted with ethyl acetate (200 ml) and brine (3×100 ml). The organic phase was collected, dried ($Na_2SO_4$), filtered and evaporated to give a brown solid (1.32 g) which was used in the next step without further purification.

APCI-MS m/z: 214.1 [$MH^+$].

Starting Material SM4

5-[Bromo(4-chlorophenyl)acetyl]-N,6-dimethyl-2-oxo-1-[3-(trifluoromethyl)-phenyl]-1,2-dihydropyridine-3-carboxamide A mixture of 5-iodo-N,6-dimethyl-2-oxo-1-[3-(trifluoromethyl)phenyl]-1,2-dihydropyridine-3-carboxamide (139 mg, 0.32 mmol), tetrakis(triphenylphosphine) palladium(0) (1.8 mg, 1.6 μmol), copper(I) iodide (0.6 mg 3.2 μmol), 1-chloro-4-ethynylbenzene (87 mg, 0.638 mmol) and DIEA (64 mg, 0.5 mmol) in acetonitrile (1.5 ml) was heated in a microwave oven to 70° C. for 0.5 h. After cooling, the reaction mixture was purified by flash chromatography to give 5-[(4-chlorophenyl)ethynyl]-N,6-dimethyl-2-oxo-1-[3-(trifluoromethyl)phenyl]-1,2-dihydropyridine-3-carboxamide (111 mg, 78%).

APCI-MS m/z: 445.3 [$MH^+$].

5-[(4-Chlorophenyl)ethynyl]-N,6-dimethyl-2-oxo-1-[3-(trifluoromethyl)phenyl]-1,2-dihydropyridine-3-carboxamide (111 mg, 0.25 mmol) was mixed with formic acid (1 ml) and heated in a microwave oven to 120° C. for 1 h. The formic acid was evaporated off and the residue was purified on an Xterra C8 column using a gradient of acetonitrile/water. Freeze drying of the mixture afforded 5-[(4-chlorophenyl)acetyl]-N,6-dimethyl-2-oxo-1-[3-(trifluoromethyl)phenyl]-1,2-dihydropyridine-3-carboxamide (77 mg, 66%).

$^1$H NMR (399.99 MHz, DMSO-$D_6$) δ 9.08 (d, J=4.8 Hz, 1H), 8.94 (s, 1H), 7.92 (d, J=9.0 Hz, 2H), 7.83 (t, J=7.8 Hz, 1H), 7.73 (d, J=8.0 Hz, 1H), 7.40 (d, J=8.5 Hz, 2H), 7.28 (d, J=8.5 Hz, 2H), 4.38 (s, 2H), 2.81 (d, J=4.8 Hz, 3H), 2.22 (s, 3H);

APCI-MS m/z: 463.0 [$MH^+$].

A solution of bromine (30 mg, 19 mmol) in acetic acid—THF was added dropwise to a solution of 5-[(4-chlorophenyl)acetyl]-N,6-dimethyl-2-oxo-1-[3-(trifluoromethyl)phenyl]-1,2-dihydropyridine-3-carboxamide (75 mg, 0.162 mmol). After the addition, stirring was continued at RT overnight. The solvents were removed and the residue was purified on an Xterra C8 column using a gradient of acetonitrile/water. Freeze drying of the mixture afforded the title compound (86 mg, 95%).

$^1$H NMR (399.988 MHz, $CDCl_3$) δ 9.06 (m, 2H), 7.84 (d, J=7.8 Hz, 1H), 7.77 (q, J=7.8 Hz, 1H), 7.53 (t, J=1.5 Hz, 2H), 7.47-7.35 (m, 4H), 6.27 (d, J=3.4 Hz, 1H), 2.96 (d, J=5.0 Hz, 3H), 2.35 (s, 3H);

APCI-MS m/z: 540.9 [$MH^+$].

Human Neutrophil Elastase Quenched-FRET Assay

The assay uses Human Neutrophil Elastase (HNE) purified from serum (Calbiochem art. 324681; Ref. Baugh, R. J. et al., 1976, Biochemistry. 15, 836-841). HNE was stored in 50 mM sodium acetate (NaOAc), 200 mM sodium chloride (NaCl), pH 5.5 with added 30% glycerol at −20° C. The protease substrate used was Elastase Substrate V Fluorogenic, MeO-Suc-AAPV-AMC (Calbiochem art. 324740; Ref. Castillo, M. J. et al., 1979, Anal. Biochem. 99, 53-64). The substrate stored in dimethyl sulphoxide (DMSO) at −20° C. The assay additions were as follows: Test compounds and controls were added to black 96-well flat-bottom plates (Greiner 655076), 1 μL in 100% DMSO, followed by 30 μL HNE in assay buffer with 0.01% Triton (trade mark) X-100 detergent. The assay buffer constitution was: 100 mM Tris(hydroxymethyl)aminomethane (TRIS) (pH 7.5) and 500 mM NaCl. The enzyme and the compounds were incubated at room temperature for 15 minutes. Then 30 μl substrate in assay buffer was added. The assay was incubated for 30 minutes at room temperature. The concentrations of HNE enzyme and substrate during the incubation were 1.7 nM and 100 μM, respectively. The assay was then stopped by adding 60 μl stop solution (140 mM acetic acid, 200 mM sodium monochloroacetate, 60 mM sodium acetate, pH 4.3). Fluorescence was measured on a Wallac 1420 Victor 2 instrument at settings: Excitation 380 nm, Emission 460 nm. $IC_{50}$ values were determined using Xlfit curve fitting using model 205.

When tested in the above screen, the compounds of the Examples gave $IC_{50}$ values for inhibition of human neutrophil elastase activity of less than 30 μM (micromolar), indicating that the compounds of the invention are expected to possess useful therapeutic properties. Specimen results are shown in the following Table:

| Compound | Inhibition of Human Neutrophil Elastase $IC_{50}$ (micromolar, μM) |
| --- | --- |
| Example 1 | 0.00021 |
| Example 3 | 0.00026 |
| Example 4 | 0.0016 |
| Example 5 | 0.00026 |
| Example 6 | 0.00093 |

The invention claimed is:

1. A compound of formula (I)

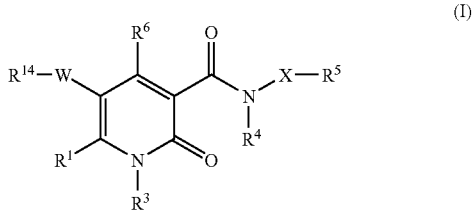

wherein $R^1$ represents hydrogen or $C_1$-$C_6$ alkyl;

W represents pyrazolyl, triazolyl, thiazolyl or oxazolyl; and wherein W is optionally substituted by at least one substituent selected from halogen, $C_1$-$C_4$ alkyl, $C_1$-$C_4$ alkoxy, CN, OH, $NO_2$, $C_1$-$C_3$ alkyl substituted by one or more F atoms, $C_1$-$C_3$ alkoxy substituted by one or more F atoms, $NR^{10}R^{11}$, C≡$CR^{15}$, $CONR^{16}R^{17}$, CHO, $C_2$-$C_4$ alkanoyl, $S(O)_xR^{18}$ and $OSO_2R^{19}$;

$R^{14}$ represents phenyl optionally substituted with at least one substituent selected from F, Cl, CN, $NO_2$ and $CF_3$;

$R^{10}$ and $R^{11}$ independently represent H, $C_1$-$C_6$ alkyl, formyl or $C_2$-$C_6$ alkanoyl; or the group —$NR^{10}R^{11}$ or —$NR^{12}R^{13}$ together represents a 5 to 7 membered azacyclic ring optionally incorporating one further heteroatom selected from O, S and $NR^{26}$;

$R^{15}$ represents H, $C_1$-$C_3$ alkyl or $Si(CH_3)_3$;

$R^{18}$ and $R^{19}$ independently represent H or $C_1$-$C_3$ alkyl; said alkyl being optionally substituted by one or more F atoms;

$R^6$ represents H or F;

$R^3$ represents phenyl or a five- or six-membered heteroaromatic ring containing 1 to 3 heteroatoms independently selected from O, S and N; said ring being optionally substituted with at least one substituent selected from halogen, $C_1$-$C_6$ alkyl, cyano, $C_1$-$C_6$ alkoxy, nitro, methylcarbonyl, $NR^{35}R^{36}$, $C_1$-$C_3$ alkyl substituted by one or more F atoms or $C_1$-$C_3$ alkoxy substituted by one or more F atoms;

$R^{35}$ and $R^{36}$ independently represent H or $C_1$-$C_3$ alkyl; said alkyl being optionally further substituted by one or more F atoms;

$R^4$ represents hydrogen or $C_1$-$C_6$ alkyl optionally substituted with at least one substituent selected from fluoro, hydroxyl and $C_1$-$C_6$ alkoxy;

X represents a single bond, O, $NR^{24}$ or a group —$C_1$-$C_6$ alkylene-Y—, wherein Y represents a single bond, oxygen atom, $NR^{24}$ or $S(O)_w$; and said alkylene being optionally further substituted by OH, halogen, CN, $NR^{37}R^{38}$, $C_1$-$C_3$ alkoxy, $CONR^{39}R^{40}$, $CO_2R^{66}$, $SO_2R^{41}$ and $SO_2NR^{42}R^{43}$;

or $R^4$ and X are joined together such that the group —$NR^4X$ together represents a 5 to 7 membered azacyclic ring optionally incorporating one further heteroatom selected from O, S and $NR^{44}$; said ring being optionally substituted by $C_1$-$C_6$ alkyl or $NR^{45}R^{46}$; said alkyl being optionally further substituted by OH;

either $R^5$ represents a monocyclic ring system selected from i) phenoxy,
ii) phenyl,
iii) a 5- or 6-membered heteroaromatic ring comprising at least one ring heteroatom selected from nitrogen, oxygen and sulphur,
iv) a saturated or partially unsaturated $C_3$-$C_6$ cycloalkyl ring, or
v) a saturated or partially unsaturated 4- to 7-membered heterocyclic ring comprising at least one ring heteroatom selected from oxygen, $S(O)_r$ and $NR^{20}$, wherein at least one of the ring carbon atoms may be optionally replaced by a carbonyl group, or $R^5$ represents a bicyclic ring system in which the two rings are independently selected from the monocyclic ring systems defined in ii), iii), iv) and v) above, wherein the two rings are either fused together, bonded directly to one another or are separated from one another by a linker group selected from oxygen, $S(O)_t$ or $C_1$-$C_6$ alkylene optionally comprising one or more internal or terminal heteroatoms selected from oxygen, sulphur and $NR^{27}$ and being optionally substituted by at least one substituent selected from hydroxyl, oxo and $C_1$-$C_6$ alkoxy, the monocyclic or bicyclic ring system being optionally substituted by at least one substituent selected from oxygen, CN, OH, $C_1$-$C_6$ alkyl, $C_1$-$C_6$ alkoxy, halogen, $NR^{47}R^{48}$, $NO_2$, $OSO_2R^{49}$, $CO_2R^{50}$, C(=NH)$NH_2$, $C(O)NR^{51}R^{52}$, $C(S)NR^{53}R^{54}$, SC(=NH)$NH_2$, $NR^{55}C$(=NH)$NH_2$, $S(O)_vR^{21}$, $SO_2NR^{56}R^{57}$, $C_1$-$C_3$ alkoxy substituted by one or more F atoms and $C_1$-$C_3$ alkyl substituted by $SO_2R^{58}$ or by one or more F atoms; said $C_1$-$C_6$ alkyl being optionally further substituted with at least one substituent selected from cyano, hydroxyl, $C_1$-$C_6$ alkoxy, $C_1$-$C_6$ alkylthio and —$C(O)NR^{22}R^{23}$;

or $R^5$ may also represent H;

$R^{20}$ represents hydrogen, $C_1$-$C_6$ alkyl, $C_1$-$C_6$ alkylcarbonyl or $C_1$-$C_6$ alkoxycarbonyl;

$R^{21}$ represents hydrogen, $C_1$-$C_6$ alkyl or $C_3$-$C_8$ cycloalkyl; said alkyl or cycloalkyl group being optionally further substituted by one or more substituents selected independently from OH, CN, $C_1$-$C_3$ alkoxy and $CONR^{59}R^{60}$;

$R^{37}$ and $R^{38}$ independently represent H, $C_1$-$C_6$ alkyl, formyl or $C_2$-$C_6$ alkanoyl;

$R^{47}$ and $R^{48}$ represent H, $C_1$-$C_6$ alkyl, formyl, $C_2$-$C_6$ alkanoyl, $S(O)_qR^{61}$ or $SO_2NR^{62}R^{63}$ said alkyl group being optionally further substituted by halogen, CN, $C_1$-$C_4$ alkoxy or $CONR^{64}R^{65}$;

$R^{41}$ and $R^{61}$ independently represent H, $C_1$-$C_6$ alkyl or $C_3$-$C_6$ cycloalkyl;

p is 0, 1 or 2;

q is 0, 1 or 2;

r is 0, 1 or 2;

t is 0, 1 or 2;

w is 0, 1 or 2;

x is 0, 1 or 2;

v is 0, 1 or 2;

$R^{16}$, $R^{17}$, $R^{22}$, $R^{23}$, $R^{24}$, $R^{26}$, $R^{27}$, $R^{39}$, $R^{40}$, $R^{42}$, $R^{43}$, $R^{44}$, $R^{45}$, $R^{46}$, $R^{49}$, $R^{50}$, $R^{51}$, $R^{52}$, $R^{53}$, $R^{54}$, $R^{55}$, $R^{56}$, $R^{57}$, $R^{58}$, $R^{59}$, $R^{60}$, $R^{62}$, $R^{63}$, $R^{64}$, $R^{65}$ and $R^{66}$ each independently represent hydrogen or $C_1$-$C_6$ alkyl;

or a pharmaceutically acceptable salt thereof.

2. The compound according to claim 1, or a pharmaceutically acceptable salt thereof, wherein the group $R^{14}$ and the 2-pyridone ring are bonded to the 5-membered ring W in a 1,2-relationship.

3. The compound according to claim 1, or a pharmaceutically acceptable salt thereof, wherein $R^3$ represents a phenyl group substituted with one or two substituents independently selected from F, Cl, CN, $NO_2$ and $CF_3$.

4. The compound according to claim 1, or a pharmaceutically acceptable salt thereof, wherein $R^5$ represents phenyl or pyridinyl substituted by —$S(O)_vR^{21}$ wherein v represents the integer 2.

5. The compound according to claim 1, or a pharmaceutically acceptable salt thereof, wherein X represents unsubstituted $C_1$-$C_2$ alkylene.

6. The compound according to claim 1, or a pharmaceutically acceptable salt thereof, wherein $R^5$ represents H.

7. The compound of formula (I) as defined in claim 1 selected from:

- 5-[1-(4-cyanophenyl)-1H-pyrazol-5-yl]-N,6-dimethyl-2-oxo-1-[3-(trifluoromethyl)phenyl]-1,2-dihydropyridine-3-carboxamide;
- 5-[1-(4-cyanophenyl)-1H-pyrazol-5-yl]-6-methyl-N-[4-(methylsulfonyl)benzyl]-2-oxo-1-[3-(trifluoromethyl)phenyl]-1,2-dihydropyridine-3-carboxamide;
- 5-[2-amino-5-(4-chlorophenyl)-1,3-thiazol-4-yl]-N,6-dimethyl-2-oxo-1-[3-(trifluoromethyl)phenyl]-1,2-dihydropyridine-3-carboxamide;
- 5-[4-(4-chlorophenyl)-1,3-oxazol-5-yl]-N,6-dimethyl-2-oxo-1-[3-(trifluoromethyl)phenyl]-1,2-dihydropyridine-3-carboxamide;
- 5-[2-amino-5-(4-cyanophenyl)-1,3-thiazol-4-yl]-N,6-dimethyl-2-oxo-1-[3-(trifluoromethyl)phenyl]-1,2-dihydropyridine-3-carboxamide;
- 1-(3-chloro-4-fluorophenyl)-5-[1-(4-cyanophenyl)-1H-pyrazol-5-yl]-N,6-dimethyl-2-oxo-1,2-dihydropyridine-3-carboxamide;
- 5-[2-(4-chloro-phenyl)-2H-pyrazol-3-yl]-6-methyl-2-oxo-1-(3-trifluoromethyl-phenyl)-1,2-dihydro-pyridine-3-carboxylic acid methylamide;
- 5-[2-(4-fluoro-phenyl)-2H-pyrazol-3-yl]-6-methyl-2-oxo-1-(3-trifluoromethyl-phenyl)-1,2-dihydro-pyridine-3-carboxylic acid methylamide;
- 5-[3-(4-cyano-phenyl)-3H-[1,2,3]triazol-4-yl]-6-methyl-2-oxo-1-(3-trifluoromethyl-phenyl)-1,2-dihydro-pyridine-3-carboxylic acid methylamide; and
- 5-[1-(4-cyanophenyl)-1H-1,2,4-triazol-5-yl]-N,6-dimethyl-2-oxo-1-[3-(trifluoromethyl)phenyl]-1,2-dihydropyridine-3-carboxamide;

or a pharmaceutically acceptable salt thereof.

8. A process for the preparation of a compound of formula (I) or a pharmaceutically acceptable salt thereof as defined in claim 1 which comprises, (a) reacting a compound of formula (II)

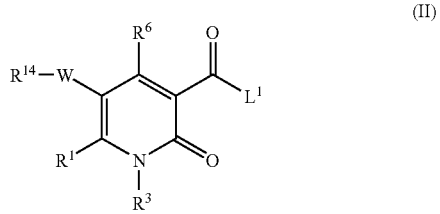

(II)

wherein $L^1$ represents a leaving group and $R^1$, $R^3$, $R^6$, $R^{14}$ and W are as defined in claim 1, with a compound of formula

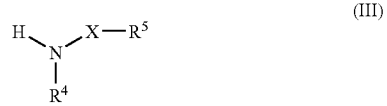

(III)

wherein X, $R^4$ and $R^5$ are as defined in claim 1; or (b) reacting a compound of formula (IV)

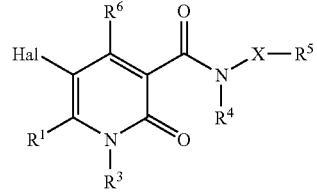

(IV)

wherein Hal represents a halogen atom and X, $R^1$, $R^3$, $R^4$, $R^5$ and $R^6$ are as defined in claim 1, with a nucleophile $R^{14}$—W-M wherein $R^{14}$ and W are as defined in claim 1 and M represents an organo-tin or organo boronic acid group; or (c) when W represents thiazolyl or oxazolyl, reacting a compound of formula (V)

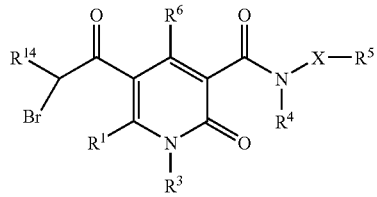

(V)

wherein X, $R^1$, $R^3$, $R^4$, $R^5$, $R^6$ and $R^{14}$ are as defined in claim 1, with thiourea or formamide respectively;

and optionally after (a), (b) or (c) carrying out one or more of the following:
- converting the compound obtained to a further compound of the invention
- forming a pharmaceutically acceptable salt of the compound.

9. A pharmaceutical composition comprising the compound of claim 1 or a pharmaceutically acceptable salt thereof in association with a pharmaceutically acceptable adjuvant, diluent or carrier.

10. The compound according to claim 1, or a pharmaceutically acceptable salt thereof, wherein $R^1$ represents a methyl group.

11. The compound according to claim 1, or a pharmaceutically acceptable salt thereof, wherein $R^3$ represents a phenyl group substituted with one or two substituents independently selected from fluorine, chlorine, cyano, nitro and trifluoromethyl.

12. The compound according to claim 1, or a pharmaceutically acceptable salt thereof, wherein X represents a group —$C_1$-$C_6$ alkylene-Y— and Y represents a single bond and the alkylene moiety is a linear or branched $C_1$-$C_4$ alkylene, optionally substituted by OH, halogen, CN or $C_1$-$C_3$ alkoxy.

13. The compound according to claim 1, or a pharmaceutically acceptable salt thereof, wherein $R^4$ is hydrogen.

* * * * *